US011547571B2

(12) United States Patent
Byrd et al.

(10) Patent No.: US 11,547,571 B2
(45) Date of Patent: Jan. 10, 2023

(54) TIBIAL PROSTHESIS WITH TIBIAL BEARING COMPONENT SECURING FEATURE

(71) Applicant: Zimmer, Inc., Warsaw, IN (US)

(72) Inventors: Brian D. Byrd, North Webster, IN (US); Kathleen Macke, Warsaw, IN (US); Dwight T Todd, Fort Wayne, IN (US); James D. Wernle, Warsaw, IN (US); Vanessa Croll, Warsaw, IN (US); Jeff Blaylock, Fort Wayne, IN (US); Abraham P. Habegger, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 353 days.

(21) Appl. No.: 16/849,394

(22) Filed: Apr. 15, 2020

(65) Prior Publication Data
US 2020/0237518 A1    Jul. 30, 2020

Related U.S. Application Data

(63) Continuation of application No. 15/915,886, filed on Mar. 8, 2018, now Pat. No. 10,675,153.
(Continued)

(51) Int. Cl.
*A61F 2/38* (2006.01)
*A61F 2/30* (2006.01)

(52) U.S. Cl.
CPC ............ *A61F 2/389* (2013.01); *A61F 2/3886* (2013.01); *A61F 2002/30401* (2013.01); *A61F 2002/30433* (2013.01); *A61F 2002/30476* (2013.01)

(58) Field of Classification Search
CPC ...... A61F 2/389; A61F 2/3886; A61F 2/3868; A61F 2/3836; A61F 2/3863; A61F 2/3895; A61F 2/3881
See application file for complete search history.

(56) References Cited

U.S. PATENT DOCUMENTS 3,774,244 A    11/1973  Walker
4,016,606 A     4/1977  Murray et al.
(Continued)

FOREIGN PATENT DOCUMENTS

AU    2011343440 B2     4/2014
AU    2011286306 B2    10/2014
(Continued)

OTHER PUBLICATIONS

"U.S. Appl. No. 15/720,866, Notice of Allowance dated Sep. 23, 2020", 7 pgs.
(Continued)

*Primary Examiner* — Alvin J Stewart
(74) *Attorney, Agent, or Firm* — Schwegman Lundberg & Woessner, P.A.

(57) ABSTRACT

According to one example, a tibial prosthesis that can include a tibial bearing component, tibial baseplate, an insert and a fastener. The tibial bearing component can have medial and lateral proximal articular surfaces and an opposing distal surface. The tibial bearing component can define at least one recess therein with the recess having an opening at a periphery of the tibial bearing component. The tibial baseplate can be coupled to the tibial bearing component on the proximal surface thereof and having a distal surface configured to be disposed on a resected proximal surface of a tibia. The insert can be configured to be disposed within the recess and can engage the tibial baseplate and the tibial bearing component. The fastener can be insertable into the
(Continued)

tibial bearing component and can be configured to retain the insert to the tibial baseplate.

20 Claims, 11 Drawing Sheets

Related U.S. Application Data

(60) Provisional application No. 62/469,924, filed on Mar. 10, 2017.

(56) References Cited

U.S. PATENT DOCUMENTS

| | | | |
|---|---|---|---|
| 4,257,129 A * | 3/1981 | Volz | A61F 2/389 623/20.33 |
| 4,340,978 A | 7/1982 | Buechel et al. | |
| 4,501,266 A | 2/1985 | McDaniel | |
| 4,568,348 A | 2/1986 | Johnson et al. | |
| 4,673,408 A | 6/1987 | Grobbelaar | |
| 4,711,639 A | 12/1987 | Grundei | |
| 4,714,474 A | 12/1987 | Brooks, Jr. et al. | |
| 4,759,767 A | 7/1988 | Lacey | |
| 4,769,040 A | 9/1988 | Wevers | |
| 4,770,661 A | 9/1988 | Oh | |
| 4,795,468 A | 1/1989 | Hodorek et al. | |
| 4,822,365 A | 4/1989 | Walker et al. | |
| 4,936,853 A | 6/1990 | Fabian et al. | |
| 4,944,756 A | 7/1990 | Kenna | |
| 4,944,757 A * | 7/1990 | Martinez | A61F 2/389 623/20.15 |
| 4,950,298 A | 8/1990 | Gustilo et al. | |
| 4,959,071 A | 9/1990 | Brown et al. | |
| 4,963,152 A | 10/1990 | Hofmann et al. | |
| 5,007,933 A | 4/1991 | Sidebotham et al. | |
| 5,047,057 A | 9/1991 | Lawes | |
| 5,047,058 A | 9/1991 | Roberts et al. | |
| 5,059,216 A | 10/1991 | Winters | |
| 5,061,271 A | 10/1991 | Van Zile | |
| 5,071,438 A | 12/1991 | Jones et al. | |
| 5,108,442 A | 4/1992 | Smith | |
| 5,116,375 A | 5/1992 | Hofmann | |
| 5,133,758 A | 7/1992 | Hollister | |
| 5,137,536 A | 8/1992 | Koshino | |
| 5,147,405 A | 9/1992 | Van Zile | |
| 5,171,283 A | 12/1992 | Pappas et al. | |
| 5,192,328 A | 3/1993 | Winters | |
| 5,194,066 A * | 3/1993 | Van Zile | A61F 2/38 623/20.15 |
| 5,197,488 A | 3/1993 | Kovacevic | |
| 5,219,362 A | 6/1993 | Tuke et al. | |
| 5,226,915 A | 7/1993 | Bertin | |
| 5,236,461 A | 8/1993 | Forte | |
| 5,246,459 A | 9/1993 | Elias | |
| 5,271,737 A | 12/1993 | Baldwin et al. | |
| 5,275,603 A | 1/1994 | Ferrante et al. | |
| 5,282,861 A | 2/1994 | Kaplan | |
| 5,282,868 A | 2/1994 | Bahler | |
| 5,282,870 A | 2/1994 | Moser et al. | |
| 5,290,313 A | 3/1994 | Heldreth | |
| 5,310,480 A | 5/1994 | Vidueira | |
| 5,326,361 A | 7/1994 | Hollister | |
| 5,344,460 A | 9/1994 | Turanyi et al. | |
| 5,344,461 A | 9/1994 | Phlipot | |
| 5,360,016 A | 11/1994 | Kovacevic | |
| 5,364,402 A | 11/1994 | Mumme et al. | |
| 5,370,699 A | 12/1994 | Hood et al. | |
| 5,387,239 A | 2/1995 | Bianco et al. | |
| 5,387,240 A | 2/1995 | Pottenger et al. | |
| 5,395,401 A | 3/1995 | Bahler | |
| 5,405,396 A | 4/1995 | Heldreth et al. | |
| 5,413,604 A | 5/1995 | Hodge | |
| 5,413,605 A | 5/1995 | Ashby et al. | |
| 5,425,775 A | 6/1995 | Kovacevic et al. | |
| 5,445,642 A | 8/1995 | McNulty et al. | |
| 5,458,637 A | 10/1995 | Hayes | |
| 5,470,354 A | 11/1995 | Hershberger et al. | |
| 5,489,311 A | 2/1996 | Cipolletti | |
| 5,507,820 A | 4/1996 | Pappas | |
| 5,549,688 A | 8/1996 | Ries et al. | |
| 5,556,433 A | 9/1996 | Gabriel et al. | |
| 5,571,194 A | 11/1996 | Gabriel | |
| 5,609,639 A | 3/1997 | Walker | |
| 5,609,641 A | 3/1997 | Johnson et al. | |
| 5,609,643 A | 3/1997 | Colleran et al. | |
| 5,609,645 A | 3/1997 | Vinciuerra | |
| 5,613,970 A | 3/1997 | Houston et al. | |
| 5,656,785 A | 8/1997 | Trainor et al. | |
| 5,658,341 A | 8/1997 | Delfosse | |
| 5,658,342 A | 8/1997 | Draganich et al. | |
| 5,658,344 A | 8/1997 | Hurlburt | |
| 5,683,470 A | 11/1997 | Johnson et al. | |
| 5,702,463 A | 12/1997 | Pothier et al. | |
| 5,702,464 A | 12/1997 | Lackey et al. | |
| 5,733,292 A | 3/1998 | Gustilo et al. | |
| 5,755,801 A | 5/1998 | Walker et al. | |
| 5,755,802 A | 5/1998 | Gerber | |
| 5,776,200 A | 7/1998 | Johnson et al. | |
| 5,782,925 A | 7/1998 | Collazo et al. | |
| 5,824,100 A | 10/1998 | Kester et al. | |
| 5,824,102 A | 10/1998 | Buscayret | |
| 5,824,103 A | 10/1998 | Williams et al. | |
| 5,871,539 A | 2/1999 | Pappas | |
| 5,871,541 A | 2/1999 | Gerber | |
| 5,871,543 A | 2/1999 | Hofmann | |
| 5,871,545 A | 2/1999 | Goodfellow et al. | |
| 5,879,394 A | 3/1999 | Ashby et al. | |
| 5,906,643 A | 5/1999 | Walker | |
| 5,911,723 A | 6/1999 | Ashby et al. | |
| 5,928,286 A | 7/1999 | Ashby et al. | |
| 5,964,808 A | 10/1999 | Blaha et al. | |
| 5,968,099 A | 10/1999 | Badorf et al. | |
| 5,976,147 A | 11/1999 | LaSalle et al. | |
| 6,004,351 A | 12/1999 | Tomita et al. | |
| 6,004,352 A * | 12/1999 | Buni | A61F 2/389 623/20.33 |
| 6,010,534 A | 1/2000 | O'neil et al. | |
| 6,013,103 A | 1/2000 | Kaufman et al. | |
| 6,039,764 A | 3/2000 | Pottenger et al. | |
| 6,068,658 A | 5/2000 | Insall et al. | |
| 6,074,425 A | 6/2000 | Pappas | |
| 6,080,195 A | 6/2000 | Colleran et al. | |
| 6,090,144 A | 7/2000 | Letot et al. | |
| 6,102,954 A | 8/2000 | Albrektsson et al. | |
| 6,102,955 A | 8/2000 | Mendes et al. | |
| 6,123,728 A * | 9/2000 | Brosnahan | A61F 2/3868 623/20.14 |
| 6,123,729 A | 9/2000 | Insall et al. | |
| 6,126,692 A * | 10/2000 | Robie | A61F 2/389 623/20.32 |
| 6,143,034 A | 11/2000 | Burrows | |
| 6,197,064 B1 | 3/2001 | Haines et al. | |
| 6,203,576 B1 | 3/2001 | Afriat et al. | |
| 6,206,927 B1 | 3/2001 | Fell et al. | |
| 6,210,443 B1 | 4/2001 | Marceaux et al. | |
| 6,217,618 B1 * | 4/2001 | Hileman | A61F 2/3868 623/20.29 |
| RE37,277 E | 7/2001 | Baldwin et al. | |
| 6,258,127 B1 | 7/2001 | Schmotzer | |
| 6,306,172 B1 | 10/2001 | O'Neil et al. | |
| 6,325,828 B1 | 12/2001 | Dennis et al. | |
| 6,379,388 B1 | 4/2002 | Ensign et al. | |
| 6,406,497 B2 | 6/2002 | Takei et al. | |
| 6,413,279 B1 | 7/2002 | Metzger et al. | |
| 6,428,577 B1 | 8/2002 | Evans | |
| 6,436,145 B1 | 8/2002 | Miller | |
| 6,485,519 B2 * | 11/2002 | Meyers | A61F 2/3868 623/20.14 |
| 6,491,726 B2 | 12/2002 | Pappas | |
| 6,506,215 B1 | 1/2003 | Letot et al. | |
| 6,506,216 B1 | 1/2003 | McCue et al. | |
| 6,558,426 B1 | 5/2003 | Masini | |
| 6,607,559 B2 | 8/2003 | Ralph et al. | |
| 6,623,526 B1 | 9/2003 | Lloyd | |

(56) References Cited

U.S. PATENT DOCUMENTS

| | | |
|---|---|---|
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |
| 6,755,864 B1 | 6/2004 | Brack et al. |
| 6,770,078 B2 | 8/2004 | Bonutti |
| 6,869,448 B2 | 3/2005 | Tuke |
| 6,916,340 B2 * | 7/2005 | Metzger .................. A61F 2/389 623/908 |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |
| 7,083,652 B2 | 8/2006 | McCue et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,105,386 B2 * | 1/2012 | Perrone, Jr. ........... A61F 2/3868 623/20.29 |
| 8,141,437 B2 | 3/2012 | Amirouche et al. |
| 8,152,853 B2 * | 4/2012 | Belcher ................ A61F 2/3886 623/20.14 |
| 8,163,028 B2 * | 4/2012 | Metzger .................. A61F 2/385 623/20.15 |
| 8,187,280 B2 | 5/2012 | May et al. |
| 8,197,549 B2 | 6/2012 | Amirouche et al. |
| 8,211,041 B2 | 7/2012 | Fisher |
| 8,245,583 B2 | 8/2012 | Stein |
| 8,268,006 B2 | 9/2012 | Meyers et al. |
| 8,317,870 B2 | 11/2012 | Wagner et al. |
| 8,328,873 B2 | 12/2012 | Metzger et al. |
| 8,366,782 B2 | 2/2013 | Wright |
| 8,491,589 B2 | 7/2013 | Fisher et al. |
| 8,506,571 B2 | 8/2013 | Chana et al. |
| RE44,476 E * | 9/2013 | Meyers ................ A61F 2/3868 623/20.15 |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 * | 12/2013 | Claypool ............. A61F 2/4684 606/88 |
| 8,613,775 B2 | 12/2013 | Wentorf et al. |
| 8,617,250 B2 * | 12/2013 | Metzger .................. A61F 2/389 623/20.32 |
| 8,628,580 B2 | 1/2014 | Sanford et al. |
| 8,690,954 B2 | 4/2014 | Parisi et al. |
| 8,740,984 B2 * | 6/2014 | Hartdegen ............. A61F 2/389 623/20.32 |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,795,282 B2 | 8/2014 | Earl et al. |
| 8,808,387 B2 | 8/2014 | Hawkins et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 8,979,936 B2 * | 3/2015 | White .................. A61F 2/3868 623/20.32 |
| 8,998,997 B2 | 4/2015 | Ries et al. |
| 9,011,459 B2 | 4/2015 | Claypool et al. |
| 9,072,607 B2 | 7/2015 | Parisi et al. |
| 9,131,945 B2 | 9/2015 | Aram et al. |
| 9,149,206 B2 | 10/2015 | Claypool et al. |
| 9,173,744 B2 | 11/2015 | Donno et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,095 B2 | 4/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 9,925,052 B2 | 3/2018 | Dai et al. |
| 10,010,330 B2 | 7/2018 | Claypool et al. |
| 10,092,407 B2 | 10/2018 | Faccioli et al. |
| 10,188,530 B2 | 1/2019 | Claypool et al. |
| 10,195,041 B2 | 2/2019 | Wentorf et al. |
| 10,265,181 B2 | 4/2019 | Wentorf et al. |
| 10,278,827 B2 | 5/2019 | Drury et al. |
| 10,413,415 B2 | 9/2019 | Parisi et al. |
| 10,470,889 B2 | 11/2019 | Wentorf et al. |
| 10,500,054 B2 | 12/2019 | Croll |
| 10,517,735 B2 * | 12/2019 | Lloyd .................. A61F 2/389 |
| 10,543,099 B2 | 1/2020 | Sanford et al. |
| 10,575,956 B2 | 3/2020 | Dai et al. |
| 10,675,153 B2 * | 6/2020 | Byrd ................... A61F 2/389 |
| 10,835,380 B2 | 11/2020 | Drury et al. |
| 10,898,337 B2 | 1/2021 | Parisi et al. |
| 11,051,948 B2 * | 7/2021 | Arnold ................ A61F 2/3845 |
| 11,160,659 B2 | 11/2021 | Drury et al. |
| 11,207,198 B2 * | 12/2021 | Oh ...................... A61F 2/3836 |
| 11,224,519 B2 | 1/2022 | Wentorf et al. |
| 11,324,598 B2 | 5/2022 | Zimmer |

(56) References Cited

U.S. PATENT DOCUMENTS

| | | |
|---|---|---|
| 11,324,599 B2 | 5/2022 | Zimmer |
| 2001/0004721 A1 | 11/2001 | Wolf |
| 2002/0058997 A1 | 5/2002 | O'connor et al. |
| 2002/0072802 A1 | 6/2002 | O'Neil et al. |
| 2002/0103541 A1* | 8/2002 | Meyers ............... A61F 2/3868 623/20.24 |
| 2002/0120340 A1 | 8/2002 | Metzger et al. |
| 2002/0161448 A1 | 10/2002 | Hayes, Jr. et al. |
| 2003/0055509 A1 | 3/2003 | Mccue et al. |
| 2003/0199985 A1 | 10/2003 | Masini |
| 2004/0019382 A1 | 1/2004 | Amirouche et al. |
| 2004/0019383 A1 | 1/2004 | Beguec |
| 2004/0034432 A1* | 2/2004 | Hughes ............... A61L 27/16 623/20.28 |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |
| 2004/0267371 A1 | 12/2004 | Hayes, Jr. et al. |
| 2005/0055102 A1 | 3/2005 | Tornier et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0177170 A1 | 8/2005 | Fisher et al. |
| 2005/0019771 A1 | 9/2005 | Naegerl |
| 2005/0209701 A1 | 9/2005 | Suguro et al. |
| 2005/0209702 A1* | 9/2005 | Todd ............... A61F 2/3868 623/20.32 |
| 2005/0246030 A1 | 11/2005 | Yao |
| 2005/0267485 A1 | 12/2005 | Cordes et al. |
| 2005/0267584 A1 | 12/2005 | Burdulis, Jr. et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor |
| 2006/0195195 A1 | 8/2006 | Burstein et al. |
| 2006/0111726 A1 | 10/2006 | Felt et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135924 A1* | 6/2007 | Verhoogen ......... A61F 2/30721 623/20.15 |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0058947 A1 | 3/2008 | Earl et al. |
| 2008/0058948 A1 | 3/2008 | Biegun et al. |
| 2008/0058271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hintermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0140212 A1 | 6/2008 | Metzger et al. |
| 2008/0161918 A1 | 7/2008 | Fankhauser et al. |
| 2008/0167722 A1* | 7/2008 | Metzger ............... A61F 2/30721 623/20.29 |
| 2008/0215156 A1 | 9/2008 | Duggal et al. |
| 2008/0243258 A1 | 10/2008 | Sancheti |
| 2008/0262624 A1 | 10/2008 | White et al. |
| 2008/0281426 A1 | 11/2008 | Fitz et al. |
| 2008/0288080 A1 | 11/2008 | Sancheti |
| 2008/0300689 A1 | 12/2008 | Mc Kinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0062806 A1 | 3/2009 | Scott et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-ganz et al. |
| 2009/0264894 A1 | 10/2009 | Wasielewski |
| 2009/0265011 A1 | 10/2009 | Mandell |
| 2009/0265013 A1 | 10/2009 | Mandell |
| 2009/0028731 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1* | 6/2010 | Lu ............... A61F 2/3886 623/20.32 |
| 2010/0191298 A1 | 7/2010 | Earl et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0292804 A1 | 11/2010 | Samuelson |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0066246 A1 | 3/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0098824 A1 | 4/2011 | Jukes et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0153026 A1 | 6/2011 | Heggendorn et al. |

(56) References Cited

U.S. PATENT DOCUMENTS

| | | |
|---|---|---|
| 2011/0190898 A1 | 8/2011 | Lenz et al. |
| 2011/0202139 A1* | 8/2011 | Metzger ............... A61F 2/3836 623/20.28 |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1* | 6/2012 | Claypool ............... A61F 2/461 623/20.32 |
| 2012/0179069 A1 | 7/2012 | Amirouche |
| 2012/0185054 A1 | 7/2012 | Maloney et al. |
| 2012/0185055 A1 | 7/2012 | Maloney et al. |
| 2012/0232429 A1 | 9/2012 | Fischer et al. |
| 2012/0290088 A1 | 11/2012 | Amirouche et al. |
| 2012/0296437 A1 | 11/2012 | Wyss et al. |
| 2012/0310246 A1 | 12/2012 | Belcher et al. |
| 2012/0310361 A1 | 12/2012 | Zubok et al. |
| 2012/0323335 A1 | 12/2012 | Parisi et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2013/0131820 A1* | 5/2013 | Wentorf ............... A61F 2/3886 623/20.32 |
| 2013/0017301 A1 | 7/2013 | Irwin |
| 2013/0226305 A1 | 8/2013 | Donno et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2013/0345820 A1 | 12/2013 | Maloney et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0025644 A1 | 1/2015 | Heggendorn et al. |
| 2015/0066150 A1 | 3/2015 | Dai et al. |
| 2015/0088140 A1 | 3/2015 | Toler et al. |
| 2015/0190243 A1 | 7/2015 | Claypool et al. |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0030053 A1 | 2/2016 | Yager et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2017/0231773 A1 | 8/2017 | Lu |
| 2017/0266011 A1 | 9/2017 | Wentorf et al. |
| 2017/0281354 A1* | 10/2017 | Soffiatti ............... A61F 2/384 |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0161166 A1 | 6/2018 | Dai et al. |
| 2018/0256346 A1 | 9/2018 | Byrd et al. |
| 2018/0325684 A1 | 11/2018 | Croll |
| 2019/0142594 A1 | 5/2019 | Yager |
| 2019/0209333 A1 | 7/2019 | Drury et al. |
| 2019/0328535 A1 | 10/2019 | Drury et al. |
| 2019/0350718 A1 | 11/2019 | Parisi et al. |
| 2020/0030106 A1 | 1/2020 | Wentorf et al. |
| 2020/0060833 A1* | 2/2020 | Arnold ............... A61F 2/30734 |
| 2020/0069433 A1 | 3/2020 | Croll |
| 2020/0113702 A1 | 4/2020 | Sanford et al. |
| 2020/0146830 A1 | 5/2020 | Dai et al. |
| 2021/0022875 A1 | 1/2021 | Drury et al. |
| 2021/0113340 A1 | 4/2021 | Parisi et al. |
| 2022/0096243 A1 | 3/2022 | Wentorf et al. |
| 2022/0233321 A1 | 7/2022 | Zimmer |
| 2022/0241081 A1* | 8/2022 | Garino ............... A61F 2/389 |

FOREIGN PATENT DOCUMENTS

| | | |
|---|---|---|
| CA | 2190029 A1 | 11/1995 |
| CA | 285607 C | 7/2016 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 9/2003 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101222886 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058446 A | 5/2011 |
| CN | 102058448 A | 5/2011 |
| CN | 102917670 A | 2/2013 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 103732186 A | 4/2014 |
| CN | 104039273 A | 9/2014 |
| CN | 104066402 A | 9/2014 |
| CN | 104093380 A | 10/2014 |
| CN | 104135969 A | 11/2014 |
| CN | 104203160 A | 12/2014 |
| CN | 104321263 A | 1/2015 |
| CN | 104379094 A | 2/2015 |
| CN | 104736105 A | 6/2015 |
| CN | 105055052 A | 11/2015 |
| CN | 105167889 A | 12/2015 |
| CN | 103118634 B | 8/2016 |
| CN | 103118636 B | 8/2016 |
| CN | 104093380 B | 8/2016 |
| CN | 103370025 B | 11/2016 |
| CN | 106073949 A | 11/2016 |
| CN | 106214292 A | 12/2016 |

(56) References Cited

FOREIGN PATENT DOCUMENTS

| | | |
|---|---|---|
| CN | 108135701 A | 6/2018 |
| CN | 106073949 B | 12/2018 |
| CN | 109310504 A | 2/2019 |
| CN | 110022798 A | 7/2019 |
| CN | 110402123 A | 11/2019 |
| CN | 110636818 A | 12/2019 |
| CN | 113317912 A | 8/2021 |
| EP | 0021421 A1 | 1/1981 |
| EP | 0303467 A2 | 2/1989 |
| EP | 0327495 A2 | 8/1989 |
| EP | 340919 A1 | 11/1989 |
| EP | 0340919 A1 | 11/1989 |
| EP | 0372811 A1 | 6/1990 |
| EP | 0306744 B1 | 4/1992 |
| EP | 0495340 A1 | 7/1992 |
| EP | 0636353 A1 | 2/1995 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0592750 B1 | 1/1999 |
| EP | 0903125 A1 | 3/1999 |
| EP | 0956836 A1 | 11/1999 |
| EP | 0956836 B1 | 11/1999 |
| EP | 1025818 A2 | 8/2000 |
| EP | 1097679 A1 | 5/2001 |
| EP | 0709074 B1 | 12/2002 |
| EP | 1327424 A1 | 7/2003 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1396240 B1 | 4/2008 |
| EP | 1604623 B1 | 6/2008 |
| EP | 1996122 A1 | 12/2008 |
| EP | 0927009 B1 | 1/2009 |
| EP | 2011455 A1 | 1/2009 |
| EP | 1696835 B1 | 2/2009 |
| EP | 1132063 A2 | 9/2009 |
| EP | 1591082 B1 | 9/2009 |
| EP | 2140838 A2 | 1/2010 |
| EP | 2140839 A1 | 1/2010 |
| EP | 2143403 A1 | 1/2010 |
| EP | 2237177 A1 | 10/2010 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 3143964 A2 | 3/2017 |
| EP | 2595574 B1 | 5/2017 |
| EP | 3111894 B1 | 12/2018 |
| FR | 2728782 A1 | 7/1996 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2345446 A | 7/2000 |
| IN | 7145DELNP2014 A | 4/2015 |
| JP | 61247449 A | 11/1986 |
| JP | 62270153 A | 11/1987 |
| JP | 06203576 A | 7/1994 |
| JP | 09289998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 2009245619 A | 10/2009 |
| JP | 2010022827 A | 2/2010 |
| JP | 2010188051 A | 9/2010 |
| JP | 2010240406 A | 10/2010 |
| JP | 2010259808 A | 11/2010 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014522292 A | 9/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| JP | 2021142355 A | 9/2021 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A2 | 3/2010 |
| WO | WO-2010045537 A1 | 4/2010 |
| WO | WO-2010075365 A2 | 7/2010 |
| WO | WO-2011043955 A1 | 4/2011 |
| WO | WO-2011063123 A2 | 5/2011 |
| WO | WO-2011071979 A2 | 6/2011 |
| WO | WO-2011072235 A2 | 6/2011 |
| WO | WO-2011110865 A2 | 9/2011 |
| WO | WO-2012004580 A1 | 1/2012 |
| WO | WO-2012018563 A1 | 2/2012 |
| WO | WO-2012018564 A1 | 2/2012 |

(56) References Cited

FOREIGN PATENT DOCUMENTS

| WO | WO-2012018565 A1 | 2/2012 |
|---|---|---|
| WO | WO-2012018566 A1 | 2/2012 |
| WO | WO-2012018567 A1 | 2/2012 |
| WO | WO-2012020460 A1 | 2/2012 |
| WO | WO-2012082628 A1 | 6/2012 |
| WO | WO-2012083280 A1 | 6/2012 |
| WO | WO-2012112698 A2 | 8/2012 |
| WO | WO-2012173706 A1 | 12/2012 |
| WO | WO-2013003433 A1 | 1/2013 |
| WO | WO-2013013094 A1 | 1/2013 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |
| WO | WO-2013077919 A1 | 5/2013 |
| WO | WO-2013115849 A1 | 8/2013 |
| WO | WO-2013148954 A1 | 10/2013 |
| WO | WO-2013148960 A1 | 10/2013 |
| WO | WO-2017053196 A1 | 3/2017 |
| WO | WO-2018165442 A1 | 9/2018 |
| WO | WO-2018208612 A1 | 11/2018 |

OTHER PUBLICATIONS

"U.S. Appl. No. 15/720,866, PTO Response to Rule 312 Communication dated Nov. 20, 2020", 2 pgs.
"U.S. Appl. No. 15/720,866, Response filed May 27, 2020 to Final Office Action dated Feb. 28, 2020", 13 pgs.
"U.S. Appl. No. 16/179,201, Advisory Action dated Jun. 25, 2021", 3 pgs.
"U.S. Appl. No. 16/179,201, Examiner Interview Summary dated Feb. 8, 2021", 3 pgs.
"U.S. Appl. No. 16/179,201, Examiner Interview Summary dated Nov. 9, 2021", 4 pgs.
"U.S. Appl. No. 16/179,201, Examiner Interview Summary dated Nov. 17, 2021", 3 pgs.
"U.S. Appl. No. 16/179,201, Final Office Action dated Apr. 20, 2021", 11 pgs.
"U.S. Appl. No. 16/179,201, Non Final Office Action dated Sep. 22, 2021", 11 pgs.
"U.S. Appl. No. 16/179,201, Non Final Office Action dated Nov. 2, 2020", 15 pgs.
"U.S. Appl. No. 16/179,201, Notice of Allowance dated Apr. 21, 2022", 9 pgs.
"U.S. Appl. No. 16/179,201, Response filed Jan. 28, 2021 to Non Final Office Action dated Nov. 2, 2020", 16 pgs.
"U.S. Appl. No. 16/179,201, Response filed Jun. 18, 2021 to Final Office Action dated Apr. 20, 2021", 16 pgs.
"U.S. Appl. No. 16/179,201, Response filed Oct. 5, 2020 to Restriction Requirement dated Aug. 7, 2020", 9 pgs.
"U.S. Appl. No. 16/179,201, Response filed Dec. 3, 2021 to Non Final Office Action dated Sep. 22, 2021", 11 pgs.
"U.S. Appl. No. 16/179,201, Restriction Requirement dated Aug. 7, 2020", 10 pgs.
"U.S. Appl. No. 16/179,201, Supplemental Response filed Feb. 19, 2021 to Non-Final Office Action dated Nov. 2, 2020", 17 pgs.
"U.S. Appl. No. 16/352,287, Final Office Action dated May 25, 2021", 8 pgs.
"U.S. Appl. No. 16/352,287, Non Final Office Action dated Dec. 10, 2020", 12 pgs.
"U.S. Appl. No. 16/352,287, Notice of Allowance dated Jun. 30, 2021", 7 pgs.
"U.S. Appl. No. 16/352,287, Response filed Feb. 22, 2021 to Non Final Office Action dated Dec. 10, 2020", 14 pgs.
"U.S. Appl. No. 16/352,287, Response filed Jun. 18, 2021 to Final Office Action dated May 25, 2021", 8 pgs.
"U.S. Appl. No. 16/352,287, Response filed Oct. 12, 2020 to Restriction Requirement dated Aug. 17, 2020", 8 pgs.
"U.S. Appl. No. 16/352,287, Restriction Requirement dated Aug. 17, 2020", 6 pgs.

"U.S. Appl. No. 16/389,381, Notice of Allowance dated Jul. 16, 2020", 5 pgs.
"U.S. Appl. No. 16/389,381, Response filed Jun. 19, 2020 to Non Final Office Action dated Mar. 30, 2020", 9 pgs.
"U.S. Appl. No. 16/530,423, Final Office Action dated Nov. 4, 2021", 11 pgs.
"U.S. Appl. No. 16/530,423, Non Final Office Action dated Mar. 3, 2022", 14 pgs.
"U.S. Appl. No. 16/530,423, Non Final Office Action dated May 17, 2021", 10 pgs.
"U.S. Appl. No. 16/530,423, Response filed Feb. 4, 2022 to Final Office Action dated Nov. 4, 2021", 15 pgs.
"U.S. Appl. No. 16/530,423, Response filed Aug. 11, 2021 to Non Final Office Action dated May 17, 2021", 15 pgs.
"U.S. Appl. No. 16/596,194, Amendment Under 1.312 Filed Dec. 7, 2021", 9 pgs.
"U.S. Appl. No. 16/596,194, Final Office Action dated May 20, 2021", 21 pgs.
"U.S. Appl. No. 16/596,194, Non Final Office Action dated Jan. 22, 2021", 19 pgs.
"U.S. Appl. No. 16/596,194, Notice of Allowance dated Sep. 9, 2021", 10 pgs.
"U.S. Appl. No. 16/596,194, PTO Response to Rule 312 Communication dated Dec. 13, 2021", 2 pgs.
"U.S. Appl. No. 16/596,194, Response filed Apr. 12, 2021 to Non Final Office Action dated Jan. 22, 2021", 15 pgs.
"U.S. Appl. No. 16/596,194, Response filed Aug. 18, 2021 to Final Office Action dated May 20, 2021", 15 pgs.
"U.S. Appl. No. 16/675,938, Non Final Office Action dated Sep. 16, 2021", 5 pgs.
"U.S. Appl. No. 16/675,938, Notice of Allowance dated Jan. 12, 2022", 8 pgs.
"U.S. Appl. No. 16/675,938, Response filed Dec. 3, 2021 to Non Final Office Action dated Sep. 16, 2021", 8 pgs.
"U.S. Appl. No. 16/675,938, Supplemental Notice of Allowability dated Feb. 1, 2022", 2 pgs.
"U.S. Appl. No. 16/715,092, Final Office Action dated Mar. 16, 2022", 8 pgs.
"U.S. Appl. No. 16/715,092, Non Final Office Action dated Sep. 22, 2021", 8 pgs.
"U.S. Appl. No. 16/715,092, Response filed Aug. 9, 2021 to Restriction Requirement dated Jun. 25, 2021", 7 pgs.
"U.S. Appl. No. 16/715,092, Response filed Dec. 10, 2021 to Non Final Office Action dated Sep. 22, 2021", 14 pgs.
"U.S. Appl. No. 16/715,092, Restriction Requirement dated Jun. 25, 2021", 6 pgs.
"U.S. Appl. No. 16/743,746, Notice of Allowance dated Jan. 13, 2022", 14 pgs.
"U.S. Appl. No. 16/743,746, Supplemental Notice of Allowability dated Jan. 27, 2022", 2 pgs.
"U.S. Appl. No. 17/068,435, Preliminary Amendment filed Nov. 13, 2020", 7 pgs.
"U.S. Appl. No. 17/134,885, Preliminary Amendment filed Jan. 18, 2021", 10 pgs.
"U.S. Appl. No. 17/545,728, Preliminary Amendment filed Jan. 7, 2022", 10 pgs.
"Australian Application Serial No. 2020204019, First Examination Report dated Jun. 18, 2021", 7 pgs.
"Australian Application Serial No. 2020204019, Response filed Jan. 11, 22 to Subsequent Examiners Report dated Nov. 16, 2021", 19 pgs.
"Australian Application Serial No. 2020204019, Response filed Aug. 19, 2021 to First Examination Report dated Jun. 18, 2021", 3 pgs.
"Australian Application Serial No. 2020204019, Response filed Oct. 15, 2021 to Subsequent Examiners Report dated Sep. 2, 2021", 22 pgs.
"Australian Application Serial No. 2020204019, Subsequent Examiners Report dated Sep. 2, 2021", 4 pgs.
"Australian Application Serial No. 2020204019, Subsequent Examiners Report dated Nov. 16, 2021", 3 pgs.

(56) References Cited

OTHER PUBLICATIONS

"Brazilian Application Serial No. BR1120130016736, Response filed Oct. 5, 2020 to Office Action dated Jun. 10, 2020", (W/ English Translation of Claims), 91 pgs.
"Canadian Application Serial No. 3,063,415, Office Action dated Jul. 13, 2020", 3 pgs.
"Canadian Application Serial No. 3,063,415, Response filed Nov. 12, 2020 to Office Action dated Jul. 13, 2020", 15 pgs.
"Chinese Application Serial No. 201880016775.4, Decision of Rejection dated Jul. 12, 2021", (W/ English Translation), 13 pgs.
"Chinese Application Serial No. 201880016775.4, Office Action dated Jan. 22, 2021", with English translation, 15 pages.
"Chinese Application Serial No. 201880031319.7, Office Action dated May 15, 2020", (W/English Translation), 12 pgs.
"Chinese Application Serial No. 201880031319.7, Office Action dated Nov. 18, 2020", (W/English Translation), 9 pgs.
"Chinese Application Serial No. 201880031319.7, Response filed Jan. 18, 2021 to Office Action dated Nov. 18, 2020", (W/ English Claims), 16 pgs.
"Chinese Application Serial No. 201880031319.7, Response filed Jul. 22, 2020 to Office Action dated May 15, 2020", (W/ English Claims), 10 pgs.
"European Application Serial No. 16189084.3, Communication Pursuant to Article 94(3) EPC dated Jul. 1, 2021", 6 pgs.
"European Application Serial No. 16189084.3, Response filed Nov. 8, 2021 to Communication Pursuant to Article 94(3) EPC dated Jul. 1, 2021", 61 pgs.
"European Application Serial No. 18726670.5, Response to Communication pursuant to Rules 161(1) and 162 EPC filed Jul. 20, 2020", 9 pgs.
"European Application Serial No. 20175535.2, Extended European Search Report dated Aug. 18, 2021", 16 pgs.
"European Application Serial No. 20175535.2, Partial European Search Report dated May 18, 2021", 18 pgs.
"European Application Serial No. 20175535.2, Response Filed Mar. 15, 2022 to Extended European Search Report dated Aug. 18, 2021", 31 pgs.
"European Application Serial No. 21178298.2, Extended European Search Report dated Mar. 1, 2022", 9 pgs.
"Indian Application Serial No. 1545/DELNP/2013, Response filed Jun. 9, 2020 to Office Action dated Dec. 9, 2019", (W/ English Claims), 78 pgs.
"Japanese Application Serial No. 2019-562605, Notification of Reasons for Refusal dated Jun. 16, 2020", (W/ English Translation), 7 pgs.
"Japanese Application Serial No. 2019-562605, Notification of Reasons for Refusal dated Nov. 10, 2020", (W/ English Translation), 5 pgs.
"Japanese Application Serial No. 2019-562605, Response filed Feb. 9, 2021 to Notification of Reasons for Refusal dated Nov. 10, 2020", (W/ English Claims), 19 pgs.
"Japanese Application Serial No. 2019-562605, Response filed Sep. 15, 2020 to Notification of Reasons for Refusal dated Jun. 16, 2020", (W/ English Claims), 15 pgs.
"Mexican Application Serial No. 2016Z001734, Response filed Aug. 31, 2021 to Office Action dated Jun. 7, 2021", (W/ English Translation of Claims), 29 pgs.
"U.S. Appl. No. 15/915,886, PTO Response to Rule 312 Communication dated May 8, 2020", 2 pgs.
"U.S. Appl. No. 15/971,743, Notice of Allowance dated Aug. 6, 2019", 8 pgs.
"U.S. Appl. No. 16/675,938, Preliminary Amendment filed Jan. 22, 2020", 7 pgs.
"Australian Application Serial No. 2012271243, Office Action dated Apr. 1, 2015", 2 pgs.
"Australian Application Serial No. 2012271243, Response filed Apr. 8, 2015 to Office Action dated Apr. 1, 2015", 4 pgs.
"Australian Application Serial No. 2012271243, Response filed Apr. 15, 2015 to Office Action dated Apr. 13, 2015", 1 pg.
"Australian Application Serial No. 2012271243, Subsequent Examiners Report dated Apr. 13, 2015", 2 pgs.
"Australian Application Serial No. 2018266322, First Examination Report dated Dec. 19, 2019", 2 pgs.
"European Application Serial No. 18711801.3, Response to Communication pursuant to Rules 161(1) and 162 EPC filed May 7, 2020", 14 pgs.
"European Application Serial No. 19171990.5, Response filed May 13, 2020 to Extended European Search Report dated Oct. 16, 2019", 31 pgs.
"International Application Serial No. PCT/US2018/031177, International Preliminary Report on Patentability dated Nov. 21, 2019", 8 pgs.
"International Application Serial No. PCT/US2018/031177, International Search Report dated Jul. 31, 2018", 6 pgs.
"International Application Serial No. PCT/US2018/031177, Written Opinion dated Jul. 31, 2018", 6 pgs.
"U.S. Appl. No. 13/087,610, Non Final Office Action dated Feb. 26, 2013", 7 pgs.
"U.S. Appl. No. 13/087,610, Notice of Allowance dated Jun. 28, 2013", 6 pgs.
"U.S. Appl. No. 13/087,610, Notice of Allowance dated Oct. 8, 2013", 7 pgs.
"U.S. Appl. No. 13/087,610, Response filed May 24, 2013 to Non Final Office Action dated Feb. 26, 2013", 15 pgs.
"U.S. Appl. No. 13/189,324, Examiner Interview Summary dated Jan. 13, 2014", 4 pgs.
"U.S. Appl. No. 13/189,324, Final Office Action dated Jul. 16, 2013", 19 pgs.
"U.S. Appl. No. 13/189,324, Non Final Office Action dated Dec. 11, 2012", 19 pgs.
"U.S. Appl. No. 13/189,324, Notice of Allowance dated Feb. 20, 2014", 8 pgs.
"U.S. Appl. No. 13/189,324, PTO Response to 312 Amendment dated May 29, 2014", 2 pgs.
"U.S. Appl. No. 13/189,324, Response filed Jan. 15, 2014 to Final Office Action dated Jul. 16, 2013", 23 pgs.
"U.S. Appl. No. 13/189,324, Response filed Jun. 10, 2013 to Non Final Office Action dated Dec. 11, 2012", 24 pgs.
"U.S. Appl. No. 13/189,328, Non Final Office Action dated Mar. 19, 2013", 10 pgs.
"U.S. Appl. No. 13/189,328, Notice of Allowance dated Oct. 8, 2013", 12 pgs.
"U.S. Appl. No. 13/189,328, PTO Response to 312 Amendment dated Dec. 13, 2013", 2 pgs.
"U.S. Appl. No. 13/189,328, Response filed Jan. 10, 2013 to Restriction Requirement dated Dec. 10, 2012", 9 pgs.
"U.S. Appl. No. 13/189,328, Response filed Jul. 18, 2013 to Non Final Office Action dated Mar. 19, 2013", 16 pgs.
"U.S. Appl. No. 13/189,328, Restriction Requirement dated Dec. 10, 2012", 6 pgs.
"U.S. Appl. No. 13/189,336, Notice of Allowance dated Sep. 13, 2013", 30 pgs.
"U.S. Appl. No. 13/189,336, PTO Response to 312 Amendment dated Nov. 25, 2013", 2 pgs.
"U.S. Appl. No. 13/189,336, Response filed Apr. 15, 2013 to Restriction Requirement dated Jan. 30, 2013", 21 pgs.
"U.S. Appl. No. 13/189,336, Response filed Jul. 17, 2013 to Restriction Requirement dated Jun. 17, 2013", 20 pgs.
"U.S. Appl. No. 13/189,336, Restriction Requirement dated Jan. 30, 2013", 5 pgs.
"U.S. Appl. No. 13/189,336, Restriction Requirement dated Jun. 17, 2013", 6 pgs.
"U.S. Appl. No. 13/189,338, Notice of Allowance dated Sep. 23, 2013", 23 pgs.
"U.S. Appl. No. 13/189,338, Response filed Apr. 15, 2013 to Restriction Requirement dated Feb. 14, 2013", 18 pgs.
"U.S. Appl. No. 13/189,338, Response filed Jul. 17, 2013 to Restriction Requirement dated Jun. 17, 2013", 16 pgs.
"U.S. Appl. No. 13/189,338, Restriction Requirement dated Feb. 14, 2013", 5 pgs.
"U.S. Appl. No. 13/189,338, Restriction Requirement dated Jun. 17, 2013", 6 pgs.

(56) References Cited

OTHER PUBLICATIONS

"U.S. Appl. No. 13/189,339, Notice of Allowance dated Sep. 20, 2013", 16 pgs.
"U.S. Appl. No. 13/189,339, Response filed Apr. 15, 2013 to Restriction Requirement dated Mar. 6, 2013", 11 pgs.
"U.S. Appl. No. 13/189,339, Response filed Jul. 17, 2013 to Restriction Requirement dated Jun. 17, 2013", 10 pgs.
"U.S. Appl. No. 13/189,339, Restriction Requirement dated Mar. 6, 2013", 6 pgs.
"U.S. Appl. No. 13/189,339, Restriction Requirement dated Jun. 17, 2013", 7 pgs.
"U.S. Appl. No. 13/229,103, Applicant Interview Summary dated Sep. 23, 2013", 2 pgs.
"U.S. Appl. No. 13/229,103, Examiner Interview Summary dated Sep. 13, 2013", 3 pgs.
"U.S. Appl. No. 13/229,103, Non Final Office Action dated Apr. 1, 2013", 18 pgs.
"U.S. Appl. No. 13/229,103, Notice of Allowance dated Sep. 18, 2013", 9 pgs.
"U.S. Appl. No. 13/229,103, Response filed Jul. 1, 2013 to Non Final Office Action dated Apr. 1, 2013", 19 pgs.
"U.S. Appl. No. 13/229,103, Supplemental Notice of Allowability dated Oct. 18, 2013", 2 pgs.
"U.S. Appl. No. 13/459,037, Final Office Action dated Sep. 23, 2013", 9 pgs.
"U.S. Appl. No. 13/459,037, Non Final Office Action dated Apr. 23, 2013", 10 pgs.
"U.S. Appl. No. 13/459,037, Notice of Allowance dated Jun. 13, 2014", 9 pgs.
"U.S. Appl. No. 13/459,037, Preliminary Amendment filed Apr. 27, 2012", 3 pgs.
"U.S. Appl. No. 13/459,037, Response filed Mar. 21, 2014 to Final Office Action dated Sep. 23, 2013", 15 pgs.
"U.S. Appl. No. 13/459,037, Response filed Mar. 28, 2013 to Restriction Requirement dated Feb. 26, 2013", 9 pgs.
"U.S. Appl. No. 13/459,037, Response filed Jul. 23, 2013 to Non Final Office Action dated Apr. 23, 2013", 19 pgs.
"U.S. Appl. No. 13/459,037, Restriction Requirement dated Feb. 26, 2013", 6 pgs.
"U.S. Appl. No. 13/459,041, Non Final Office Action dated Jan. 15, 2014", 16 pgs.
"U.S. Appl. No. 13/459,041, Non Final Office Action dated Sep. 9, 2014", 14 pgs.
"U.S. Appl. No. 13/459,041, Notice of Allowance dated Apr. 2, 2015", 10 pgs.
"U.S. Appl. No. 13/459,041, Preliminary Amendment dated Apr. 27, 2012", 7 pgs.
"U.S. Appl. No. 13/459,041, PTO Response to Rule 312 Communication dated Jun. 9, 2015", 2 pgs.
"U.S. Appl. No. 13/459,041, Response filed May 15, 2014 to Non-Final Office Action dated Jan. 15, 2014", 24 pgs.
"U.S. Appl. No. 13/459,041, Response filed Sep. 23, 2013 to Restriction Requirement dated Jul. 25, 2013", 18 pgs.
"U.S. Appl. No. 13/459,041, Response filed Dec. 9, 2014 to Non-Final Office Action dated Sep. 9, 2014", 23 pgs.
"U.S. Appl. No. 13/459,041, Restriction Requirement dated Jul. 25, 2013", 9 pgs.
"U.S. Appl. No. 13/459,048, Non Final Office Action dated Jul. 11, 2013", 6 pgs.
"U.S. Appl. No. 13/459,048, Notice of Allowance dated Nov. 26, 2013", 10 pgs.
"U.S. Appl. No. 13/459,048, Preliminary Amendment filed Apr. 27, 2012", 7 pgs.
"U.S. Appl. No. 13/459,048, Response filed Nov. 11, 2013 to Non-Final Office Action dated Jul. 11, 2013", 16 pgs.
"U.S. Appl. No. 13/459,056, Examiner Interview Summary dated Dec. 26, 2013", 3 pgs.
"U.S. Appl. No. 13/459,056, Non Final Office Action dated Jul. 25, 2013", 11 pgs.
"U.S. Appl. No. 13/459,056, Notice of Allowance dated Feb. 20, 2014", 5 pgs.
"U.S. Appl. No. 13/459,056, Preliminary Amendment filed Apr. 27, 2012", 7 pgs.
"U.S. Appl. No. 13/459,056, PTO Response to Rule 312 Communication dated May 22, 2014", 2 pgs.
"U.S. Appl. No. 13/459,056, Response filed Jan. 24, 2014 to Non-Final office Action dated Jul. 25, 2013", 27 pgs.
"U.S. Appl. No. 13/459,056, Response filed Apr. 8, 2013 to Restriction Requirement dated Mar. 6, 2013", 15 pgs.
"U.S. Appl. No. 13/459,056, Restriction Requirement dated Mar. 6, 2013", 6 pgs.
"U.S. Appl. No. 13/593,339, Non Final Office Action dated Oct. 4, 2013", 7 pgs.
"U.S. Appl. No. 13/593,339, Notice of Allowance dated Feb. 14, 2014", 9 pgs.
"U.S. Appl. No. 13/593,339, Preliminary Amendment filed Aug. 23, 2012", 6 pgs.
"U.S. Appl. No. 13/593,339, Response filed Jan. 31, 2014 to Non-Final Office Action dated Oct. 4, 2013", 19 pgs.
"U.S. Appl. No. 13/593,339, Response filed Aug. 30, 2013 to Restriction Requirement dated Aug. 1, 2013", 14 pgs.
"U.S. Appl. No. 13/593,339, Restriction Requirement dated Aug. 1, 2013", 5 pgs.
"U.S. Appl. No. 13/593,339, Supplemental Notice of Allowability dated Mar. 31, 2014", 2 pgs.
"U.S. Appl. No. 13/594,543, Corrected Notice of Allowance dated Mar. 16, 2016", 2 pgs.
"U.S. Appl. No. 13/594,543, Examiner Interview Summary dated Jan. 22, 2016", 3 pgs.
"U.S. Appl. No. 13/594,543, Final Office Action dated Jul. 17, 2014", 12 pgs.
"U.S. Appl. No. 13/594,543, Final Office Action dated Nov. 20, 2015", 28 pgs.
"U.S. Appl. No. 13/594,543, Non Final Office Action dated Jun. 19, 2015", 30 pgs.
"U.S. Appl. No. 13/594,543, Non Final Office Action dated Dec. 26, 2013", 15 pgs.
"U.S. Appl. No. 13/594,543, Non-Final Office Action dated Jan. 9, 2015", 23 pgs.
"U.S. Appl. No. 13/594,543, Notice of Allowance dated Mar. 1, 2016", 9 pgs.
"U.S. Appl. No. 13/594,543, Preliminary Amendment filed Aug. 24, 2012", 4 pgs.
"U.S. Appl. No. 13/594,543, Response filed Feb. 8, 2016 to Final Office Action dated Nov. 20, 2015", 17 pgs.
"U.S. Appl. No. 13/594,543, Response filed Apr. 7, 2015 to Non-Final Office Action dated Jan. 9, 2015", 27 pgs.
"U.S. Appl. No. 13/594,543, Response filed May 7, 2014 to Non-Final office Action dated Dec. 26, 2013", 17 pgs.
"U.S. Appl. No. 13/594,543, Response filed Sep. 21, 2015 to Non-Final Office Action dated Jun. 19, 2015", 25 pgs.
"U.S. Appl. No. 13/594,543, Response filed Oct. 11, 2013 to Restriction Requirement dated Sep. 12, 2013", 8 pgs.
"U.S. Appl. No. 13/594,543, Response filed Dec. 17, 2014 to Final Office Action dated Jul. 17, 2014", 15 pgs.
"U.S. Appl. No. 13/594,543, Restriction Requirement dated Sep. 12, 2013", 5 pgs.
"U.S. Appl. No. 13/819,116, Advisory Action dated Jan. 5, 2016", 3 pgs.
"U.S. Appl. No. 13/819,116, Corrected Notice of Allowance dated Oct. 21, 2016", 2 pgs.
"U.S. Appl. No. 13/819,116, Examiner Interview Summary dated Apr. 18, 2016", 11 pgs.
"U.S. Appl. No. 13/819,116, Final Office Action dated Jul. 26, 2016", 6 pgs.
"U.S. Appl. No. 13/819,116, Final Office Action dated Oct. 21, 2015", 15 pgs.
"U.S. Appl. No. 13/819,116, Non Final Office Action dated Feb. 17, 2016", 15 pgs.
"U.S. Appl. No. 13/819,116, Non Final Office Action dated Jun. 2, 2015", 14 pgs.

(56) References Cited

OTHER PUBLICATIONS

"U.S. Appl. No. 13/819,116, Notice of Allowance dated Sep. 29, 2016", 5 pgs.

"U.S. Appl. No. 13/819,116, Preliminary Amendment filed Feb. 26, 2013", 8 pgs.

"U.S. Appl. No. 13/819,116, Response filed Mar. 27, 2015 to Restriction Requirement dated Feb. 12, 2015", 11 pgs.

"U.S. Appl. No. 13/819,116, Response filed Apr. 29, 2016 to Non Final Office Action dated Feb. 17, 2016", 17 pgs.

"U.S. Appl. No. 13/819,116, Response filed Jul. 16, 2015 to Non Final Office Action dated Jun. 2, 2015", 22 pgs.

"U.S. Appl. No. 13/819,116, Response filed Sep. 14, 2016 Final Office Action dated Jul. 26, 2016", 10 pgs.

"U.S. Appl. No. 13/819,116, Response filed Dec. 15, 2015 to Final Office Action dated Oct. 21, 2015", 16 pgs.

"U.S. Appl. No. 13/819,116, Restriction Requirement dated Feb. 12, 2015", 7 pgs.

"U.S. Appl. No. 13/836,586, Express Abandonment filed May 30, 2014", 1 pg.

"U.S. Appl. No. 13/836,665, Examiner Interview Summary dated Jul. 17, 2014", 4 pgs.

"U.S. Appl. No. 13/836,665, Final Office Action dated Jul. 25, 2014", 25 pgs.

"U.S. Appl. No. 13/836,665, Non Final Office Action dated Jan. 30, 2014", 21 pgs.

"U.S. Appl. No. 13/836,665, Notice of Allowance dated Jun. 9, 2015", 10 pgs.

"U.S. Appl. No. 13/836,665, Response filed Jan. 23, 2015 to Final Office Action dated Jul. 25, 2014", 25 pgs.

"U.S. Appl. No. 13/836,665, Response filed May 30, 2014 to Non-Final Office Action dated Jan. 30, 2014", 21 pgs.

"U.S. Appl. No. 13/837,294, Final Office Action dated Apr. 25, 2016", 7 pgs.

"U.S. Appl. No. 13/837,294, Final Office Action dated Jun. 2, 2016", 7 pgs.

"U.S. Appl. No. 13/837,294, Non Final Office Action dated Dec. 10, 2015", 8 pgs.

"U.S. Appl. No. 13/837,294, Notice of Allowance dated Aug. 25, 2016", 5 pgs.

"U.S. Appl. No. 13/837,294, Response filed Mar. 4, 2016 to Non Final Office Action dated Dec. 10, 2015", 16 pgs.

"U.S. Appl. No. 13/837,294, Response filed Aug. 3, 2016 to Final Office Action dated Jun. 2, 2016", 7 pgs.

"U.S. Appl. No. 13/837,294, Response filed Oct. 12, 2015 to Restriction Requirement dated Aug. 24, 2015", 9 pgs.

"U.S. Appl. No. 13/837,294, Restriction Requirement dated Aug. 24, 2015", 6 pgs.

"U.S. Appl. No. 13/837,774, Examiner Interview Summary dated Jul. 22, 2014", 4 pgs.

"U.S. Appl. No. 13/837,774, Final Office Action dated Mar. 17, 2016", 14 pgs.

"U.S. Appl. No. 13/837,774, Final Office Action dated Jul. 28, 2014", 17 pgs.

"U.S. Appl. No. 13/837,774, Non Final Office Action dated Feb. 10, 2014", 33 pgs.

"U.S. Appl. No. 13/837,774, Non Final Office Action dated Sep. 18, 2015", 16 pgs.

"U.S. Appl. No. 13/837,774, Response filed Jan. 28, 2015 to Final Office Action dated Jul. 28, 2014", 16 pgs.

"U.S. Appl. No. 13/837,774, Response filed Jun. 10, 2014 to Non-Final Office Action dated Feb. 20, 2014", 29 pgs.

"U.S. Appl. No. 13/837,774, Response filed Jul. 7, 2015 to Restriction Requirement dated May 20, 2015", 10 pgs.

"U.S. Appl. No. 13/837,774, Response filed Dec. 16, 2015 to Non Final Office Action dated Sep. 18, 2015", 17 pgs.

"U.S. Appl. No. 13/837,774, Restriction Requirement dated May 20, 2015", 6 pgs.

"U.S. Appl. No. 14/034,076, Appeal Brief Filed Apr. 18, 2016", 21 pgs.

"U.S. Appl. No. 14/034,076, Final Office Action dated Dec. 21, 2015", 11 pgs.

"U.S. Appl. No. 14/034,076, Non Final Office Action dated Jun. 24, 2015", 11 pgs.

"U.S. Appl. No. 14/034,076, Notice of Allowance dated Oct. 28, 2016", 7 pgs.

"U.S. Appl. No. 14/034,076, Response filed Nov. 16, 2015 to Non Final Office Action dated Jun. 24, 2015", 13 pgs.

"U.S. Appl. No. 14/034,937, Appeal Brief Filed Sep. 9, 2015", 41 pgs.

"U.S. Appl. No. 14/034,937, Appeal Decision mailed May 30, 2017", 34 pgs.

"U.S. Appl. No. 14/034,937, Final Office Action dated Jun. 5, 2015", 22 pgs.

"U.S. Appl. No. 14/034,937, Non Final Office Action dated Jan. 2, 2015", 21 pgs.

"U.S. Appl. No. 14/034,937, Notice of Allowance dated Aug. 30, 2017", 14 pgs.

"U.S. Appl. No. 14/034,937, Preliminary Amendment filed Sep. 24, 2013", 3 pgs.

"U.S. Appl. No. 14/034,937, PTO Response to Rule 312 Communication dated Oct. 10, 2017", 2 pqs.

"U.S. Appl. No. 14/034,937, Response filed Mar. 30, 2015 to Non-Final Office Action", 24 pgs.

"U.S. Appl. No. 14/034,937, Response filed Oct. 27, 2014 to Restriction Requirement dated Sep. 11, 2014", 12 pgs.

"U.S. Appl. No. 14/034,937, Restriction Requirement dated Sep. 11, 2014", 6 pgs.

"U.S. Appl. No. 14/034,937, Supplemental Preliminary Amendment filed Oct. 24, 2013", 11 pgs.

"U.S. Appl. No. 14/034,944, Non Final Office Action dated Mar. 3, 2015", 16 pgs.

"U.S. Appl. No. 14/034,944, Notice of Allowance dated Aug. 28, 2015", 7 pgs.

"U.S. Appl. No. 14/034,944, Preliminary Amendment filed Sep. 24, 2013", 3 pgs.

"U.S. Appl. No. 14/034,944, Response filed Jun. 23, 2015 to Non Final Office Action dated Mar. 3, 2015", 15 pgs.

"U.S. Appl. No. 14/034,944, Response filed Dec. 15, 2014 to Restriction Requirement dated Oct. 14, 2014", 12 pgs.

"U.S. Appl. No. 14/034,944, Restriction Requirement dated Oct. 14, 2014", 6 pgs.

"U.S. Appl. No. 14/034,944, Supplemental Preliminary Amendment filed Oct. 24, 2013", 11 pgs.

"U.S. Appl. No. 14/034,954, Advisory Action dated Aug. 25, 2015", 3 pgs.

"U.S. Appl. No. 14/034,954, Final Office Action dated Jun. 1, 2015", 26 pgs.

"U.S. Appl. No. 14/034,954, Non Final Office Action dated Dec. 19, 2014", 25 pgs.

"U.S. Appl. No. 14/034,954, Notice of Allowance dated Nov. 20, 2015", 11 pgs.

"U.S. Appl. No. 14/034,954, Preliminary Amendment filed Sep. 24, 2013", 3 pgs.

"U.S. Appl. No. 14/034,954, Response filed Mar. 17, 2015 to Non Final Office Action dated Dec. 19, 2014", 21 pgs.

"U.S. Appl. No. 14/034,954, Response filed Aug. 3, 2015 to Final Office Action dated Jun. 1, 2015", 19 pgs.

"U.S. Appl. No. 14/034,954, Response filed Aug. 31, 2015 to Advisory Action dated Aug. 25, 2015", 21 pgs.

"U.S. Appl. No. 14/034,954, Response filed Oct. 27, 2014 to Restriction Requirement dated Aug. 25, 2014", 11 pgs.

"U.S. Appl. No. 14/034,954, Restriction Requirement dated Aug. 25, 2014", 7 pgs.

"U.S. Appl. No. 14/034,954, Supplemental Preliminary Amendment filed Oct. 25, 2013", 8 pgs.

"U.S. Appl. No. 14/034,963, Final Office Action dated Apr. 13, 2015", 22 pgs.

"U.S. Appl. No. 14/034,963, Final Office Action dated Oct. 13, 2015", 11 pgs.

"U.S. Appl. No. 14/034,963, Non Final Office Action dated Jul. 1, 2015", 15 pgs.

(56) References Cited

OTHER PUBLICATIONS

"U.S. Appl. No. 14/034,963, Non Final Office Action dated Nov. 21, 2014", 19 pgs.
"U.S. Appl. No. 14/034,963, Notice of Allowance dated Dec. 18, 2015", 5 pgs.
"U.S. Appl. No. 14/034,963, Preliminary Amendment filed Sep. 24, 2013", 3 pgs.
"U.S. Appl. No. 14/034,963, Response filed Mar. 20, 2015 to Non-Final Office Action dated Nov. 21, 2014", 20 pgs.
"U.S. Appl. No. 14/034,963, Response filed Jun. 19, 2015 to Final Office Action dated Apr. 13, 2015", 17 pgs.
"U.S. Appl. No. 14/034,963, Response filed Sep. 30, 2015 to Non Final Office Action dated Jul. 1, 2015", 14 pgs.
"U.S. Appl. No. 14/034,963, Response filed Nov. 20, 2015 to Final Office Action dated Oct. 13, 2015", 12 pgs.
"U.S. Appl. No. 14/063,032, Non Final Office Action dated Jun. 20, 2014", 6 pgs.
"U.S. Appl. No. 14/063,032, Notice of Allowance dated Dec. 19, 2014", 6 pgs.
"U.S. Appl. No. 14/063,032, Preliminary Amendment filed Oct. 25, 2013", 3 pgs.
"U.S. Appl. No. 14/063,032, Response filed Oct. 20, 2014 to Non-Final Office Action dated Jun. 20, 2014", 9 pgs.
"U.S. Appl. No. 14/063,593, Advisory Action dated Aug. 19, 2016", 3 pgs.
"U.S. Appl. No. 14/063,593, Final Office Action dated Jun. 9, 2016", 10 pgs.
"U.S. Appl. No. 14/063,593, Non Final Office Action dated Jan. 25, 2016", 9 pgs.
"U.S. Appl. No. 14/063,593, Non Final Office Action dated Nov. 30, 2016", 12 pgs.
"U.S. Appl. No. 14/063,593, Notice of Allowance dated May 2, 2017", 5 pgs.
"U.S. Appl. No. 14/063,593, Notice of Allowance dated May 25, 2017", 5 pgs.
"U.S. Appl. No. 14/063,593, Preliminary Amendment filed Oct. 25, 2013", 3 pgs.
"U.S. Appl. No. 14/063,593, Response filed Jan. 4, 2016 to Restriction Requirement dated Nov. 6, 2015", 6 pgs.
"U.S. Appl. No. 14/063,593, Response filed Feb. 24, 2017 to Non Final Office Action dated Nov. 30, 2016", 17 pgs.
"U.S. Appl. No. 14/063,593, Response filed Apr. 20, 2016 to Non Final Office Action dated Jan. 25, 2016", 17 pgs.
"U.S. Appl. No. 14/063,593, Response filed Aug. 11, 2016 to Final Office Action dated Jun. 9, 2016", 10 pgs.
"U.S. Appl. No. 14/063,593, Restriction Requirement dated Nov. 6, 2015", 6 pgs.
"U.S. Appl. No. 14/181,033, Non Final Office Action dted May 1, 2015", 5 pgs.
"U.S. Appl. No. 14/181,033, Notice of Allowance dated Jul. 17, 2015", 10 pgs.
"U.S. Appl. No. 14/181,033, Response filed Jun. 22, 2015 to Non-Final Office Action dated May 1, 2015", 11 pgs.
"U.S. Appl. No. 14/278,805, Notice of Allowance dated Dec. 1, 2015", 8 pgs.
"U.S. Appl. No. 14/278,805, Supplemental Notice of Allowability dated Jan. 21, 2016", 2 pgs.
"U.S. Appl. No. 14/284,028, Non Final Office Action dated Jul. 7, 2015", 17 pgs.
"U.S. Appl. No. 14/284,028, Notice of Allowance dated Nov. 6, 2015", 5 pgs.
"U.S. Appl. No. 14/284,028, Response filed Oct. 6, 2015 to Non Final Office Action dated Jul. 7, 2015", 15 pgs.
"U.S. Appl. No. 14/284,028, Supplemental Notice of Allowability dated Feb. 26, 2016", 5 pgs.
"U.S. Appl. No. 14/284,028, Supplemental Preliminary Amendment filed Jul. 8, 2014", 13 pgs.
"U.S. Appl. No. 14/284,144, Final Office Action dated Aug. 7, 2015", 13 pgs.
"U.S. Appl. No. 14/284,144, Non Final Office Action dated Mar. 25, 2015", 26 pgs.
"U.S. Appl. No. 14/284,144, Notice of Allowance dated Oct. 29, 2015", 8 pgs.
"U.S. Appl. No. 14/284,144, Preliminary Amendment filed May 21, 2014", 3 pgs.
"U.S. Appl. No. 14/284,144, Response filed Oct. 9, 2015 to Final Office Action dated Aug. 7, 2015", 13 pgs.
"U.S. Appl. No. 14/284,144, Response filed Jun. 23, 2015 to Non Final Office Action dated Mar. 25, 2015", 22 pgs.
"U.S. Appl. No. 14/284,144, Supplemental Preliminary Amendment filed Jul. 3, 2014", 10 pgs.
"U.S. Appl. No. 14/304,009, Notice of Allowance dated Nov. 16, 2016", 7 pgs.
"U.S. Appl. No. 14/304,009, Preliminary Amendment Filed Jul. 31, 2014", 7 pgs.
"U.S. Appl. No. 14/471,440, Notice of Allowance dated Nov. 13, 2017", 9 pgs.
"U.S. Appl. No. 14/471,440, Response filed Aug. 16, 2017 to Restriction Requirement dated Jun. 30, 2017", 8 pgs.
"U.S. Appl. No. 14/471,440, Restriction Requirement dated Jun. 30, 2017", 6 pgs.
"U.S. Appl. No. 14/490,153, Final Office Action dated Apr. 15, 2015", 18 pgs.
"U.S. Appl. No. 14/490,153, Non Final Office Action dated Nov. 12, 2014", 9 pgs.
"U.S. Appl. No. 14/490,153, Notice of Allowance dated Aug. 14, 2015", 10 pgs.
"U.S. Appl. No. 14/490,153, Preliminary Amendment filed Sep. 18, 2014", 3 pgs.
"U.S. Appl. No. 14/490,153, Response filed Feb. 18, 2015 to Non-Final Office Action dated Nov. 12, 2014", 14 pgs.
"U.S. Appl. No. 14/490,153, Response filed Jul. 7, 2015 to Final Office Action dated Apr. 15, 2015", 14 pgs.
"U.S. Appl. No. 14/660,217, Corrected Notice of Allowance dated May 26, 2016", 3 pgs.
"U.S. Appl. No. 14/660,217, Non Final Office Action dated Dec. 17, 2015", 8 pgs.
"U.S. Appl. No. 14/660,217, Notice of Allowance dated Apr. 26, 2016", 5 pgs.
"U.S. Appl. No. 14/660,217, Preliminary Amendment filed Mar. 18, 2015", 9 pgs.
"U.S. Appl. No. 14/660,217, Response filed Mar. 23, 2016 to Non Final Office Action dated Dec. 17, 2015", 14 pgs.
"U.S. Appl. No. 14/740,690, Non Final Office Action dated Dec. 7, 2016", 19 pgs.
"U.S. Appl. No. 14/740,690, Notice of Allowability dated Aug. 29, 2017", 2 pgs.
"U.S. Appl. No. 14/740,690, Notice of Allowance dated Jun. 13, 2017", 9 pgs.
"U.S. Appl. No. 14/740,690, Response filed Mar. 3, 2017 to Non Final Office Action dated Dec. 7, 2016", 14 pgs.
"U.S. Appl. No. 14/791,952, Corrected Notice of Allowance dated Jul. 21, 2017", 2 pgs.
"U.S. Appl. No. 14/791,952, Final Office Action dated Mar. 31, 2017", 8 pgs.
"U.S. Appl. No. 14/791,952, Final Office Action dated Sep. 1, 2016", 17 pgs.
"U.S. Appl. No. 14/791,952, Non Final Office Action dated Apr. 21, 2016", 12 pgs.
"U.S. Appl. No. 14/791,952, Non Final Office Action dated Dec. 29, 2016", 12 pgs.
"U.S. Appl. No. 14/791,952, Notice of Allowance dated May 30, 2017", 7 pgs.
"U.S. Appl. No. 14/791,952, Preliminary Amendment filed Jul. 7, 2015", 7 pgs.
"U.S. Appl. No. 14/791,952, Response filed Mar. 20, 2017 to Non Final Office Action dated Dec. 29, 2016", 12 pgs.
"U.S. Appl. No. 14/791,952, Response filed May 17, 2017—to Final Office Action dated Mar. 31, 2017", 10 pgs.
"U.S. Appl. No. 14/791,952, Response filed Jul. 15, 2016 to Non Final Office Action dated Apr. 21, 2016", 18 pgs.

(56) References Cited

OTHER PUBLICATIONS

"U.S. Appl. No. 14/791,952, Response filed Nov. 21, 2016 to Final Office Action dated Sep. 1, 2016", 15 pgs.
"U.S. Appl. No. 14/833,385, Examiner Interview Summary dated Dec. 27, 2017", 3 pgs.
"U.S. Appl. No. 14/833,385, Final Office Action dated Nov. 13, 2017", 9 pgs.
"U.S. Appl. No. 14/833,385, Non Final Office Action dated Jun. 19, 2017", 10 pgs.
"U.S. Appl. No. 14/833,385, Preliminary Amendment filed Aug. 25, 2015", 6 pgs.
"U.S. Appl. No. 14/833,385, Response filed May 12, 2017 to Restriction Requirement dated Mar. 17, 2017", 8 pgs.
"U.S. Appl. No. 14/833,385, Response filed Sep. 18, 2017 to Non Final Office Action dated Jun. 19, 2017", 14 pgs.
"U.S. Appl. No. 14/833,385, Restriction Requirement dated Mar. 17, 2017", 6 pgs.
"U.S. Appl. No. 14/918,721, Final Office Action dated Oct. 20, 2016", 5 pgs.
"U.S. Appl. No. 14/918,721, Non Final Office Action dated Jun. 16, 2016", 6 pgs.
"U.S. Appl. No. 14/918,721, Notice of Allowance dated Feb. 1, 2017", 9 pgs.
"U.S. Appl. No. 14/918,721, Preliminary Amendment filed Oct. 23, 2015", 8 pgs.
"U.S. Appl. No. 14/918,721, PTO Response to Rule 312 Communication dated Mar. 17, 2017", 2 pgs.
"U.S. Appl. No. 14/918,721, Response filed Sep. 12, 2016 to Non Final Office Action dated Jun. 16, 2016", 12 pgs.
"U.S. Appl. No. 14/918,721, Response filed Dec. 13, 2016 to Final Office Action dated Oct. 20, 2016", 9 pgs.
"U.S. Appl. No. 14/926,281, Non Final Office Action dated Jun. 21, 2017", 17 pgs.
"U.S. Appl. No. 14/926,281, Notice of Allowance dated Nov. 16, 2017", 9 pgs.
"U.S. Appl. No. 14/926,281, Preliminary Amendment filed Oct. 30, 2015", 8 pgs.
"U.S. Appl. No. 14/926,281, Response filed Sep. 18, 2017 to Non Final Office Action dated Jun. 21, 2017", 11 pgs.
"U.S. Appl. No. 15/003,091, Preliminary Amendment filed Jan. 22, 2016", 12 pgs.
"U.S. Appl. No. 15/003,091, Non Final Office Action dated Jun. 20, 2017", 14 pgs.
"U.S. Appl. No. 15/003,091, Notice of Allowance dated Nov. 6, 2017", 8 pgs.
"U.S. Appl. No. 15/003,091, PTO Response to Rule 312 Communication dated Jan. 23, 2018", 2 pgs.
"U.S. Appl. No. 15/003,091, Response filed Sep. 20, 2017 to Non Final Office Action dated Jun. 20, 2017", 17 pgs.
"U.S. Appl. No. 15/045,799, Non Final Office Action dated Nov. 1, 2016", 8 pgs.
"U.S. Appl. No. 15/045,799, Notice of Allowance dated Mar. 10, 2017", 10 pgs.
"U.S. Appl. No. 15/045,799, Preliminary Amendment filed Feb. 18, 2016", 9 pgs.
"U.S. Appl. No. 15/045,799, PTO Response to Rule 312 Communication dated Apr. 18, 2017", 2 pgs.
"U.S. Appl. No. 15/045,799, Response filed Feb. 1, 2017 to Non Final Office Action dated Nov. 1, 2016", 15 pgs.
"U.S. Appl. No. 15/062,252, Preliminary Amendment filed Mar. 9, 2016", 8 pgs.
"U.S. Appl. No. 15/062,262, Non Final Office Action dated Jul. 22, 2016", 12 pgs.
"U.S. Appl. No. 15/062,262, Notice of Allowance dated Jan. 31, 2017", 5 pgs.
"U.S. Appl. No. 15/062,262, PTO Response to Rule 312 Communication dated Mar. 7, 2017", 2 pgs.
"U.S. Appl. No. 15/062,262, Response filed Oct. 24, 2016 to Non Final Office Action dated Jul. 22, 2016", 13 pgs.
"U.S. Appl. No. 15/177,734, Non Final Office Action dated Feb. 10, 2017", 21 pgs.
"U.S. Appl. No. 15/177,734, Notice of Allowance dated May 17, 2017", 7 pgs.
"U.S. Appl. No. 15/177,734, Preliminary Amendment filed Jun. 22, 2016", 8 pgs.
"U.S. Appl. No. 15/177,734, Response filed Apr. 19, 2017 to Non Final Office Action dated Feb. 10, 2017", 22 pgs.
"U.S. Appl. No. 15/211,812, Non Final Office Action dated Jan. 27, 2017", 5 pgs.
"U.S. Appl. No. 15/211,812, Notice of Allowance dated May 31, 2017", 5 pgs.
"U.S. Appl. No. 15/211,812, Preliminary Amendment filed Sep. 8, 2016", 8 pgs.
"U.S. Appl. No. 15/211,812, Response filed Apr. 19, 2017 to Non Final Office Action dated Jan. 27, 2017", 9 pgs.
"U.S. Appl. No. 15/267,793, Non Final Office Action dated Jun. 14, 2018", 12 pgs.
"U.S. Appl. No. 15/267,793, Notice of Allowability dated Jan. 17, 2019", 2 pgs.
"U.S. Appl. No. 15/267,793, Notice of Allowance dated Dec. 21, 2018", 5 pgs.
"U.S. Appl. No. 15/267,793, Response Filed Apr. 11, 2018 to Restriction Requirement dated Feb. 16, 2018", 8 pgs.
"U.S. Appl. No. 15/267,793, Response filed Aug. 22, 2018 Non Final Office Action dated Jun. 14, 2018", 16 pgs.
"U.S. Appl. No. 15/267,793, Restriction Requirement dated Feb. 16, 2018", 7 pgs.
"U.S. Appl. No. 15/424,328, Non Final Office Action dated Jun. 23, 2017", 5 pgs.
"U.S. Appl. No. 15/424,328, Notice of Allowance dated Oct. 16, 2017", 6 pgs.
"U.S. Appl. No. 15/424,328, Preliminary Amendment filed Feb. 28, 2017", 10 pgs.
"U.S. Appl. No. 15/424,328, Response filed Sep. 20, 2017 to Non Final Office Action dated Jun. 23, 2017", 9 pgs.
"U.S. Appl. No. 15/435,620, Final Office Action dated Dec. 15, 2017", 9 pgs.
"U.S. Appl. No. 15/435,620, Non Final Office Action dated Jul. 26, 2017", 10 pgs.
"U.S. Appl. No. 15/435,620, Notice of Allowance dated Mar. 13, 2018", 5 pgs.
"U.S. Appl. No. 15/435,620, Preliminary Amendment filed Mar. 20, 2017", 7 pgs.
"U.S. Appl. No. 15/435,620, Response filed Feb. 12, 2018 to Final Office Action dated Dec. 15, 2017", 9 pgs.
"U.S. Appl. No. 15/435,620, Response filed Oct. 25, 2017 to Non Final Office Action dated Jul. 26, 2017", 13 pgs.
"U.S. Appl. No. 15/616,561, Non Final Office Action dated Aug. 9, 2018", 8 pgs.
"U.S. Appl. No. 15/616,561, Notice of Allowability dated Feb. 12, 2019", 2 pgs.
"U.S. Appl. No. 15/616,561, Notice of Allowance dated Dec. 10, 2018", 7 pgs.
"U.S. Appl. No. 15/616,561, Preliminary Amendment filed Jun. 8, 2017", 7 pgs.
"U.S. Appl. No. 15/616,561, Response filed Nov. 8, 2018 to Non Final Office Action dated Aug. 9, 2018", 11 pgs.
"U.S. Appl. No. 15/703,678, Non Final Office Action dated Apr. 8, 2019", 11 pgs.
"U.S. Appl. No. 15/703,678, Notice of Allowance dated Sep. 17, 2019", 7 pgs.
"U.S. Appl. No. 15/703,678, Preliminary Amendment filed Sep. 28, 2017", 9 pgs.
"U.S. Appl. No. 15/703,678, Response Filed Jan. 3, 2019 to Restriction Requirement dated Nov. 5, 2018", 8 pgs.
"U.S. Appl. No. 15/703,678, Response filed Jul. 3, 2019 to Non-Final Office Action dated Apr. 8, 2019", 20 pgs.
"U.S. Appl. No. 15/703,678, Restriction Requirement dated Nov. 5, 2018", 6 pgs.
"U.S. Appl. No. 15/703,692, Corrected Notice of Allowability dated Jul. 8, 2019", 2 pgs.

(56) References Cited

OTHER PUBLICATIONS

"U.S. Appl. No. 15/703,692, Non Final Office Action dated Jan. 14, 2019", 11 pgs.
"U.S. Appl. No. 15/703,692, Notice of Allowance dated May 7, 2019", 5 pgs.
"U.S. Appl. No. 15/703,692, Preliminary Amendment filed Sep. 28, 2017", 9 pgs.
"U.S. Appl. No. 15/703,692, Response filed Apr. 4, 2019 to Non Final Office Action dated Jan. 14, 2019", 11 pgs.
"U.S. Appl. No. 15/703,698, Corrected Notice of Allowability dated Dec. 18, 2018", 2 pgs.
"U.S. Appl. No. 15/703,698, Non Final Office Action dated Apr. 6, 2018", 7 pgs.
"U.S. Appl. No. 15/703,698, Notice of Allowance dated Sep. 12, 2018", 5 pgs.
"U.S. Appl. No. 15/703,698, Preliminary Amendment filed Sep. 28, 2017", 8 pgs.
"U.S. Appl. No. 15/703,698, Response filed Jul. 6, 2018 to Non Final Office Action dated Apr. 6, 2018", 10 pgs.
"U.S. Appl. No. 15/703,713, Non Final Office Action dated Mar. 27, 2018", 29 pgs.
"U.S. Appl. No. 15/703,713, Notice of Allowance dated Sep. 25, 2018", 11 pgs.
"U.S. Appl. No. 15/703,713, Response Filed Jun. 15, 2018 to Non-Final Office Action dated Mar. 27, 2018", 16 pgs.
"U.S. Appl. No. 15/703,713, Preliminary Amendment filed Sep. 28, 2017", 7 pgs.
"U.S. Appl. No. 15/720,866, Final Office Action dated Feb. 28, 2020", 10 pgs.
"U.S. Appl. No. 15/720,866, Non Final Office Action dated Sep. 9, 2019", 12 pgs.
"U.S. Appl. No. 15/720,866, Response filed Jan. 9, 2020 to Non Final Office Action dated Sep. 9, 2019", 11 pgs.
"U.S. Appl. No. 15/720,866, Response filed Jul. 10, 2019 to Restriction Requirement dated May 14, 2019", 10 pgs.
"U.S. Appl. No. 15/720,866, Response filed Nov. 13, 2017 to Non Final Office Action dated Sep. 14, 2017", 10 pgs.
"U.S. Appl. No. 15/720,866, Restriction Requirement dated May 14, 2019", 7 pgs.
"U.S. Appl. No. 15/720,866, Preliminary Amendment filed Nov. 13, 2017", 9 pgs.
"U.S. Appl. No. 15/827,654, Examiner Interview Summary dated Apr. 26, 2019", 4 pgs.
"U.S. Appl. No. 15/827,654, Final Office Action dated Feb. 19, 2019", 19 pgs.
"U.S. Appl. No. 15/827,654, Non Final Office Action dated Sep. 7, 2018", 21 pgs.
"U.S. Appl. No. 15/827,654, Notice of Allowance dated Jul. 8, 2019", 8 pgs.
"U.S. Appl. No. 15/827,654, Preliminary Amendment filed Dec. 22, 2017", 11 pgs.
"U.S. Appl. No. 15/827,654, Response Filed May 20, 2019 to Final Office Action dated Feb. 19, 2019", 17 pgs.
"U.S. Appl. No. 15/827,654, Response filed Jun. 6, 2018 to Restriction Requirement dated Apr. 6, 2018", 11 pgs.
"U.S. Appl. No. 15/827,654, Response filed to Non Final Office Action dated Sep. 7, 2018", 24 pgs.
"U.S. Appl. No. 15/827,654, Restriction Requirement dated Apr. 6, 2018", 6 pgs.
"U.S. Appl. No. 15/890,735, Notice of Allowance dated Oct. 29, 2019", 11 pgs.
"U.S. Appl. No. 15/915,886, Non Final Office Action dated Aug. 2, 2019", 9 pgs.
"U.S. Appl. No. 15/915,886, Notice of Allowance dated Jan. 16, 2020", 9 pgs.
"U.S. Appl. No. 15/915,886, Response Filed Nov. 4, 2019 to Non-Final Office Action dated Aug. 2, 2019", 8 pgs.
"U.S. Appl. No. 16/389,381, Non Final Office Action dated Mar. 30, 2020", 9 pgs.
"U.S. Appl. No. 16/530,423, Preliminary Amendment filed Aug. 28, 2019", 7 pgs.
"U.S. Appl. No. 16/596,194, Preliminary Amendment Filed Nov. 14, 2019", 8 pgs,.
"U.S. Appl. No. 16/715,092, Preliminary Amendment filed Mar. 19, 2020", 10 pgs.
"U.S. Appl. No. 16/743,746, Preliminary Amendment filed Mar. 19, 2020".
"Australian Application Serial No. 2011286306, First Examiner Report dated Jun. 19, 2013", 4 pgs.
"Australian Application Serial No. 2011286306, Response filed Jun. 3, 2014 to First Examiner Report dated Jun. 19, 2013", 16 pgs.
"Australian Application Serial No. 2011286307, First Examiner Report dated Oct. 17, 2013", 2 pgs.
"Australian Application Serial No. 2011286307, Response filed May 21, 2014 to First Examiner Report dated Oct. 17, 2013", 16 pgs.
"Australian Application Serial No. 2011286308, First Examiner Report dated Jun. 21, 2013", 4 pgs.
"Australian Application Serial No. 2011286308, Response filed Jun. 6, 2014 First Examiner Report dated Jun. 21, 2013", 19 pgs.
"Australian Application Serial No. 2011286309, First Examiner Report dated Jun. 21, 2013", 3 pgs.
"Australian Application Serial No. 2011286309, Response filed Jun. 10, 2014 to First Examiner Report dated Jun. 21, 2013", 4 pgs.
"Australian Application Serial No. 2011343440, First Examiner Report dated Feb. 17, 2014", 3 pgs.
"Australian Application Serial No. 2011343440, Response filed Mar. 21, 2014 to Office Action dated Feb. 17, 2014", 1 pg.
"Australian Application Serial No. 2012341026, First Examiner Report dated Jul. 14, 2014", 2 pgs.
"Australian Application Serial No. 2012341026, Response filed Nov. 21, 2014 to First Examiner Report dated Jul. 14, 2014", 1 pg.
"Australian Application Serial No. 2012341026, Statement of Proposed Amendment filed Jun. 18, 2014", 25 pgs.
"Australian Application Serial No. 2012368262, First Examiner Report dated Nov. 2, 2016", 4 pgs.
"Australian Application Serial No. 2012368262, Response filed Jan. 17, 2017 to Office Action dated Nov. 2, 2016", 21 pgs.
"Australian Application Serial No. 2012368262, Response filed May 15, 2017 to Subsequent Examiners Report, dated Mar. 16, 2017", 2 pgs.
"Australian Application Serial No. 2012368262, Subsequent Examiners Report dated Mar. 16, 2017", 3 pgs.
"Australian Application Serial No. 2013238046, First Examiner Report dated Nov. 26, 2015", 2 pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2011 to First Examiner Report dated Oct. 17, 2016", 9 pgs.
"Australian Application Serial No. 2014250709, First Examiner Report dated Dec. 21, 2015", 3 pgs.
"Australian Application Serial No. 2014250709, Response filed May 4, 2016 to First Examiner Report dated Dec. 21, 2015", 12 pgs.
"Australian Application Serial No. 2014250709, Subsequent Examiners Report dated May 31, 2016", 6 pgs.
"Australian Application Serial No. 2014250710, First Examiner Report dated Dec. 11, 2015", 7 pgs.
"Australian Application Serial No. 2014250710, Response filed Mar. 22, 2016 to First Examiner Report dated Dec. 11, 2015", 18 pgs.
"Australian Application Serial No. 2014250710, Response filed May 4, 2016 to Subsequent Examiners Report dated Mar. 23, 2016", 15 pgs.
"Australian Application Serial No. 2014250710, Subsequent Examiners Report dated Mar. 23, 2016", 3 pgs.
"Australian Application Serial No. 2014250711, First Examiner Report dated Feb. 12, 2016", 7 pgs.
"Australian Application Serial No. 2014250711, Response filed Apr. 27, 2016 to First Examiner Report dated Feb. 12, 2016", 32 pgs.

(56) References Cited

OTHER PUBLICATIONS

"Australian Application Serial No. 2015201511, First Examination Report dated Apr. 18, 2016", 2 pgs.
"Australian Application Serial No. 2015201511, Response filed Jun. 30, 2016 to First Examiner Report dated Apr. 18, 2016", 12 pgs.
"Australian Application Serial No. 2015238820, First Examination Report dated May 30, 2017", 3 pgs.
"Australian Application Serial No. 2015238820, Response filed Jul. 12, 2017 to First Examination Report dated May 30, 2017", 12 pgs.
"Australian Application Serial No. 2016225911, First Examiners Report dated Jun. 2, 2017", 3 pgs.
"Australian Application Serial No. 2016225911, Response filed Aug. 22, 2017 to First Examiners Report, dated Jun. 2, 2017", 18 pgs.
"Australian Application Serial No. 2017235987, First Examination Report dated Nov. 1, 2018", 4 pgs.
"Australian Application Serial No. 2017251736, First Examiners Report dated Oct. 31, 2017", 2 pgs.
"Bi-Cruciate Stabilized Knee System", Design Rationale, Smith & Nephew Journal, (2006), 20 pgs.
"Brazil Application Serial No. BR1120130016698, Office Action dated Aug. 27, 2019", (with English translation), 8 pages.
"Brazil Application Serial No. BR1120130016698, Response filed Dec. 9, 2019 to Office Action dated Aug. 27, 2019", w/ English Claims, 22 pgs.
"Brazil Application Serial No. BR1120130016736, Office Action dated Aug. 27, 2019", (with English translation), 8 pages.
"Brazil Application Serial No. BR1120130016736, Response filed Dec. 9, 2019 to Office Action dated Aug. 27, 2019", w/ English Claims, 25 pgs.
"Canadian Application Serial No. 2,806,321, Office Action dated Jan. 15, 2018", 3 pgs.
"Canadian Application Serial No. 2,806,321, Response filed Jan. 22, 2018 to Office Action dated Jan. 15, 2018", 7 pgs.
"Canadian Application Serial No. 2,806,321, Response filed Dec. 6, 2017 to Office Action dated Jun. 15, 2017", 12 pgs.
"Canadian Application Serial No. 2,806,325, Office Action dated Mar. 14, 2016", 4 pgs.
"Canadian Application Serial No. 2,806,325, Response filed Sep. 14, 2016 to Office Action dated Mar. 14, 2016", 17 pgs.
"Canadian Application Serial No. 2,806,326, Examiner's Rule 30(2) Requisition dated Sep. 20, 2018", 4 pgs.
"Canadian Application Serial No. 2,806,326, Office Action dated Feb. 8, 2018", 4 pgs.
"Canadian Application Serial No. 2,806,326, Office Action dated Jun. 19, 2017", 3 pgs.
"Canadian Application Serial No. 2,806,326, Response Filed Mar. 20, 2019 to Examiner's Rule 30(2) Requisition dated Sep. 20, 2018", 4 pgs.
"Canadian Application Serial No. 2,806,326, Response filed Jul. 20, 2018 to Office Action dated Feb. 8, 2018", 12 pgs.
"Canadian Application Serial No. 2,821,927, Office Action dated Jan. 25, 2018", 6 pgs.
"Canadian Application Serial No. 2,821,927, Response filed Jul. 18, 2018 to Office Action dated Jan. 25, 2018", 10 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2014", 14 pgs.
"Canadian Application Serial No. 2,856,070, Preliminary Amendment filed May 25, 2015", 27 pgs.
"Canadian Application Serial No. 2,856,571 Response filed Jan. 22, 2015 to Office Action dated Jul. 22, 2014", 24 pgs.
"Canadian Application Serial No. 2,856,571, Office Action dated Jul. 22, 2014", 2 pgs.
"Canadian Application Serial No. 2,863,375, Office Action dated Apr. 20, 2018", 3 pgs.
"Canadian Application Serial No. 2,863,375, Response filed Oct. 22, 2018 Office Action dated Apr. 20, 2018", 12 pgs.
"Canadian Application Serial No. 2,868,825, Office Action dated Dec. 27, 2018", 3 pgs.
"Canadian Application Serial No. 2,956,119, Examiner's Rule 30(2) Requisition dated Sep. 27, 2018", 4 pgs.
"Canadian Application Serial No. 2,956,119, Office Action dated Jan. 22, 2018", 3 pgs.
"Canadian Application Serial No. 2,956,119, Response Filed Mar. 27, 2019 to Examiner's Rule 30(2) Reguisition dated Sep. 27, 2018", 7 pgs.
"Canadian Application Serial No. 2,989,184, Office Action dated Oct. 1, 2018", 4 pgs.
"Canadian Application Serial No. 2,989,184, Response filed Apr. 1, 2019 to Office Action dated Oct. 1, 2018", 10 pgs.
"Canadian Application Serial No. 2,806,321, Office Action dated Jun. 15, 2017", 3 pgs.
"Chinese Application Serial No. 201180045673.3, Office Action dated Feb. 14, 2016", (W/English Translation), 17 pgs.
"Chinese Application Serial No. 201180045673.3, Office Action dated Mar. 29, 2015", (W/English Translation), 6 pgs.
"Chinese Application Serial No. 201180045673.3, Office Action dated Aug. 12, 2015", (W/English Translation), 7 pgs.
"Chinese Application Serial No. 201180045673.3, Response filed Jun. 19, 2015 to Office Action dated Mar. 29, 2015", (W/ English translation of claims), 11 pgs.
"Chinese Application Serial No. 201180045673.3, Response filed 10-27-2015 to Office Action dated Aug. 12, 2015", (W/ English translation of claims), 9 pgs.
"Chinese Application Serial No. 201180045681.8, Office Action dated Jan. 22, 2015", (W/English Translation), 11 pgs.
"Chinese Application Serial No. 201180045681.8, Response filed May 14, 2015 to Office Action dated Jan. 22, 2015", W/ English Claims, 17 pgs.
"Chinese Application Serial No. 201180045683.7, Office Action dated Mar. 9, 2015", (W/ English Translation), 6 pgs.
"Chinese Application Serial No. 201180045683.7, Response filed Jul. 14, 2015 to Office Action dated Mar. 9, 2015", (W/ English translation of claims), 30 pgs.
"Chinese Application Serial No. 201180045689.4, Office Action dated Jan. 5, 2015", (W/English Translation), 4 pgs.
"Chinese Application Serial No. 201180045689.4, Office Action dated Feb. 2, 2016", w/English Translation, 11 pgs.
"Chinese Application Serial No. 201180045689.4, Office Action dated Aug. 5, 2015", (W/English Translation), 11 pgs.
"Chinese Application Serial No. 201180045689.4, Response filed May 1, 2015 to Office Action dated Jan. 5, 2015", W/ English Claims, 13 pgs.
"Chinese Application Serial No. 201180067430.X, Office Action dated Aug. 28, 2014", (W/English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/English Translation), 18 pgs.
"Chinese Application Serial No. 201180067757.7, Office Action dated Jun. 1, 2016", (W/English Translation), 10 pgs.
"Chinese Application Serial No. 201180067757.7, Office Action dated Nov. 16, 2015", (W/English Translation), 17 pgs.
"Chinese Application Serial No. 201180067757.7, Response filed Jan. 27, 2016 to Office Action dated Nov. 16, 2015", (W/ English Translation of Claims), 12 pgs.
"Chinese Application Serial No. 201180067757.7, Response filed Jul. 10, 2015 to Office Action dated Mar. 2, 2015", (W/ English Translation), 13 pgs.
"Chinese Application Serial No. 201180067757.7, Response filed Aug. 11, 2016 to Office Action dated Jun. 1, 2016", (W/ English Translation of Claims), 9 pgs.
"Chinese Application Serial No. 201180067757.7, Voluntary Amendment dated Feb. 14, 2014", (W/ English Translation of Claims), 8 pgs.
"Chinese Application Serial No. 201280067473.2, Office Action dated Feb. 1, 2016", (W/English Translation), 4 pgs.

(56) References Cited

OTHER PUBLICATIONS

"Chinese Application Serial No. 201280067473.2, Office Action dated May 20, 2015", (W/English Translation), 15 pgs.
"Chinese Application Serial No. 201280067473.2, Office Action dated Nov. 20, 2015", W/English Translation of Claims, 7 pgs.
"Chinese Application Serial No. 201280067473.2, Response filed Apr. 7, 2016 to Office Action dated Feb. 1, 2016", (W/ English translation of claims), 11 pgs.
"Chinese Application Serial No. 201280067473.2, Response filed Sep. 7, 2015 to Office Action dated May 20, 2015", (W/ English translation of claims), 12 pgs.
"Chinese Application Serial No. 201280067473.2, Response filed Dec. 4, 2015 to Office Action dated Nov. 20, 2015", w/English Claims, 11 pgs.
"Chinese Application Serial No. 201280067481.7, Office Action dated Sep. 30, 2015", (W/English Translation), 7 pgs.
"Chinese Application Serial No. 201280071940.9, Office Action dated Jul. 22, 2015", (W/English Translation), 13 pgs.
"Chinese Application Serial No. 201280071940.9, Preliminary Amendment filed Mar. 23, 2015", W/ English Claims, 11 pgs.
"Chinese Application Serial No. 201380028572.4, Office Action dated Aug. 13, 2015", (W/English Translation), 16 pgs.
"Chinese Application Serial No. 201380028683.5, Office Action dated Jun. 27, 2016", (W/English Translation), 8 pgs.
"Chinese Application Serial No. 201380028683.5, Office Action dated Nov. 4, 2015", (W/English Translation), 16 pgs.
"Chinese Application Serial No. 201380028683.5, Office Action dated Dec. 30, 2016", (W/English Translation), 4 pgs.
"Chinese Application Serial No. 201380028683.5, Response filed Feb. 8, 2017 to Office Action dated Dec. 30, 2016", (W/ English Translation), 13 pgs.
"Chinese Application Serial No. 201380028683.5, Response filed Mar. 18, 2016 to Office Action dated Nov. 4, 2015", (W/ English Translation of Claims), 11 pgs.
"Chinese Application Serial No. 201380028683.5, Response filed Sep. 6, 2016 to Office Action dated Jun. 27, 2016", (W/ English Translation of Claims), 11 pgs.
"Chinese Application Serial No. 201510394094.X, Office Action dated May 24, 2017", (W/ English Translation), 11 pgs.
"Chinese Application Serial No. 201510394094.X, Office Action dated Aug. 30, 2016", (W/English Translation), 14 pgs.
"Chinese Application Serial No. 201510394094.X, Office Action dated Nov. 3, 2017", (W/English Translation), 10 pgs.
"Chinese Application Serial No. 201510394094.X, Response filed Jan. 16, 2017 to Office Action dated Aug. 30, 2016", (W/ English Translation of Claims), 11 pgs.
"Chinese Application Serial No. 201510394094.X, Response filed Jan. 18, 2018 to Office Action dated Nov. 3, 2017", (W/ English Claims), 10 pgs.
"Chinese Application Serial No. 201510394094.X, Response filed Jul. 10, 2017 to Office Action dated May 24, 2017", (W/ English Translation), 10 pgs.
"Chinese Application Serial No. 201510640436.1, Office Action dated Sep. 28, 2016", (W/English Translation), 13 pgs.
"Chinese Application Serial No. 201510640436.1, Response filed Feb. 16, 2017 to Office Action dated Sep. 28, 2016", (W/ English Translation), 18 pgs.
"Chinese Application Serial No. 201610634595.5, Office Action dated Apr. 20, 2018", (W/English Translation), 8 pgs.
"Chinese Application Serial No. 201610634595.5, Office Action dated Jun. 21, 2017", w/English Translation, 9 pgs.
"Chinese Application Serial No. 201610634595.5, Response filed Jun. 4, 2018 to Office Action dated Apr. 20, 2018", (W/ English Translation of Claims), 8 pgs.
"Chinese Application Serial No. 201610634595.5, Response filed Nov. 3, 2017 to Office Action dated Jun. 21, 2017", w/English Claims, 8 pgs.
"Chinese Application Serial No. 201610685172.6, Office Action dated Apr. 10, 2017", (W/English Translation), 11 pgs.
"Chinese Application Serial No. 201610685172.6, Office Action dated Sep. 28, 2017", (W/English Translation), 9 pgs.
"Chinese Application Serial No. 201610685172.6, Response filed Dec. 13, 2017 to Office Action dated Sep. 28, 2017", (W/ English Claims), 13 pgs.
"Chinese Application Serial No. 201680061268.3, Office Action dated Apr. 24, 2019", (W/English Translation), 11 pgs.
"Chinese Application Serial No. 201680061268.3, Response filed Aug. 21, 2019 to Office Action dated Apr. 24, 2019", (W/ English Claims), 8 pgs.
"Complete Knee Solution Surgical Technique for the CR-Flex Fixed Bearing Knee", Zimmer Nexgen, (2003), 22 pgs.
"European Application Serial No. 11738918.9, Examination Notification Art. 94(3) dated Oct. 23, 2014", 5 pgs.
"European Application Serial No. 11738918.9, Preliminary Amendment dated Sep. 24, 2013", 11 pgs.
"European Application Serial No. 1138918.9, Response filed Mar. 2, 2015 to Examination Notification Art. 94(3) dated Oct. 23, 2014", 14 pgs.
"European Application Serial No. 11738919.7, Examination Notification Art. 94(3) dated Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) dated Jul. 7, 2014", 14 pgs.
"European Application Serial No. 11738920.5, Communication Pursuant to Article 94(3) EPC dated Mar. 15, 2016", 4 pgs.
"European Application Serial No. 11738920.5, Preliminary Amendment dated Sep. 24, 2013", 9 pgs.
"European Application Serial No. 11738920.5, Response filed Jul. 25, 2016 to Communication Pursuant to Article 94(3) EPC dated Mar. 15, 2016", 6 pgs.
"European Application Serial No. 11738920.5, Response filed Sep. 24, 2013 to Communication pursuant to Rules 161(2) and 162 EPC dated Mar. 15, 2013", 22 pgs.
"European Application Serial No. 11758060.5, Communication Pursuant to Article 94(3) EPC dated Jul. 12, 2016", 3 pgs.
"European Application Serial No. 11758060.5, Communication Pursuant to Article 94(3) EPC dated Dec. 11, 2015", 4 pgs.
"European Application Serial No. 11758060.5, Preliminary Amendment filed Nov. 4, 2013", 15 pgs.
"European Application Serial No. 11758060.5, Response filed Apr. 21, 2016 to Communication Pursuant to Article 94(3) EPC dated Dec. 11, 2015", 16 pgs.
"European Application Serial No. 11758060.5, Response filed Nov. 15, 2016 to Communication Pursuant to Article 94(3) EPC dated Jul. 12, 2016", 23 pgs.
"European Application Serial No. 11802835.6, Communication Pursuant to Article 94(3) EPC dated Dec. 11, 2017", 4 pgs.
"European Application Serial No. 11802835.6, Response filed Apr. 23, 2018 to Office Action dated Dec. 11, 2017", 16 pgs.
"European Application Serial No. 11808493.8, Communication Pursuant to Article 94(3) EPC dated Dec. 7, 2015", 4 pgs.
"European Application Serial No. 11808493.8, Examination Notification Art. 9 4(3) dated Feb. 20, 2015", 6 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493.8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art. 94(3) dated Feb. 20, 2015", 13 pgs.
"European Application Serial No. 11815029.1, Communication Pursuant to Article 94(3) EPC dated Sep. 29, 2016", 4 pgs.
"European Application Serial No. 11815029.1, Extended European Search Report dated Dec. 10, 2013", 8 pgs.
"European Application Serial No. 11815029.1, Response filed Apr. 10, 2017 to Communication Pursuant to Article 94(3) EPC dated Sep. 29, 2016", 22 pgs.

(56) References Cited

OTHER PUBLICATIONS

"European Application Serial No. 11815029.1, Response filed Jul. 21, 2014 Extended European Search Report dated Dec. 10, 2013", 15 pgs.
"European Application Serial No. 12718882.9, Communication Pursuant to Article 94(3) EPC dated Dec. 1, 2015", 11 pgs.
"European Application Serial No. 12718882.9, Response filed Feb. 10, 2015 to Communication Pursuant to Rules 161(1) and 162 EPC dated Jul. 31, 2014", 11 pgs.
"European Application Serial No. 12718882.9, Response filed Apr. 11, 2016 to Communication Pursuant to Article 94(3) EPC dated Dec. 1, 2015", 12 pgs.
"European Application Serial No. 12718883.7, Communication Pursuant to Article 94(3) EPC dated Dec. 2, 2015", 4 pgs.
"European Application Serial No. 12718883.7, Communication Pursuant to Rules 161(1) and 162 EPC dated Jul. 31, 2014", 2 pgs.
"European Application Serial No. 12718883.7, Intention to Grant dated May 20, 2016", 5 pgs.
"European Application Serial No. 12718883.7, Response filed Feb. 10, 2015 to Communication Pursuant to Rules 161(1) and 162 EPC dated Jul. 31, 2014", 16 pgs.
"European Application Serial No. 12718883.7, Response filed Apr. 12, 2016 to Communication Pursuant to Article 94(3) EPC dated Dec. 2, 2015", 30 pgs.
"European Application Serial No. 12719236.7 Response filed Feb. 9, 2015 to Communication Pursuant to Rules 161(1) and 162 EPC dated Jul. 30, 2014", 10 pgs.
"European Application Serial No. 12719236.7, Decision to Grant dated Feb. 18, 2016", 3 pgs.
"European Application Serial No. 12719236.7, Office Action dated Aug. 27, 2015", 7 pgs.
"European Application Serial No. 12720352.9 Response filed Feb. 9, 2015 to Communication Pursuant to Rules 161(1) and 162 EPC dated Jul. 30, 2014", 10 pgs.
"European Application Serial No. 12756058.9, Communication Pursuant to Article 94(3) EPC dated Feb. 18, 2019", 4 pgs.
"European Application Serial No. 12756058.9, Office Action dated Jan. 17, 2017", 5 Pgs.
"European Application Serial No. 12756058.9, Preliminary Amendment filed Apr. 20, 2015", 12 pgs.
"European Application Serial No. 12756058.9, Response filed May 26, 2017 to Office Action dated Jan. 17, 2017", 16 pgs.
"European Application Serial No. 12756058.9, Response filed Jun. 28, 2019 to Communication Pursuant to Article 94(3) EPC dated Feb. 18, 2019", 21 pgs.
"European Application Serial No. 12756869.9 Response filed Feb. 10, 2015 to Communication Pursuant to Rule 161(1) and 162 EPC dated Jul. 31, 2014", 14 pgs.
"European Application Serial No. 12756869.9, Examination Notification Art. 94(3) dated Jul. 2, 2015", 4 pgs.
"European Application Serial No. 12756869.9, Response filed Nov. 12, 2015 to Examination Notification Art. 94(3) dated Jul. 2, 2015", 28 pgs.
"European Application Serial No. 13716636.9, Communication Pursuant to Article 9 4(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Mar. 27, 2017 to Communication Pursuant to Article 94(3) EPC dated Nov. 17, 2016", 15 pgs.
"European Application Serial No. 13716636.9, Response filed Jun. 22, 2015 to Communication pursuant to Rules 161(1) and 162 EPC dated Dec. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"European Application Serial No. 15160934.4, Communication Pursuant to Article 94(3) EPC dated Apr. 26, 2018", 5 pgs.
"European Application Serial No. 15160934.4, Extended European Search Report dated Jun. 1, 2016", 8 pgs.
"European Application Serial No. 15160934.4, Response filed Aug. 30, 2018 to Communication Pursuant to Article 94(3) EPC dated Apr. 26, 2018", 63 pgs.
"European Application Serial No. 15160934.4, Response filed Dec. 21, 2016 to Extended European Search Report dated Jun. 1, 2016", 5 pgs.
"European Application Serial No. 15174394.5, Extended European Search Report dated Mar. 21, 2016", 8 pgs.
"European Application Serial No. 15174394.5, Response filed Nov. 18, 2016 to Extended European Search Report dated Mar. 21, 2016", 12 pgs.
"European Application Serial No. 15191781.2, Communication Pursuant to Article 94(3) EPC dated Jan. 8, 2018", 4 pgs.
"European Application Serial No. 15191781.2, Extended European Search Report dated Mar. 1, 2017", 8 pgs.
"European Application Serial No. 15191781.2, Response filed May 17, 2018 to Communication Pursuant to Article 94(3) EPC dated Jan. 8, 2018", 58 pgs.
"European Application Serial No. 15191781.2, Response filed Sep. 28, 2017 to Extended European Search Report dated Mar. 1, 2017", 14pgs.
"European Application Serial No. 16156228.5, Extended European Search Report dated May 11, 2017", 5 pgs.
"European Application Serial No. 16183635.8, Extended European Search Report dated Jun. 30, 2017", 9 pgs.
"European Application Serial No. 16183635.8, Response filed Mar. 27, 2018 to Extended European Search Report dated Jun. 30, 2017", 8 pgs.
"European Application Serial No. 16189084.3, Extended European Search Report dated Oct. 9, 2017", 9 pgs.
"European Application Serial No. 16189084.3, Response filed May 10, 2018 to Extended European Search Report dated Oct. 9, 2017", 20 pgs.
"European Application Serial No. 16770657.1, Communication Pursuant to Article 94(3) EPC dated May 20, 2019", 3 pgs.
"European Application Serial No. 16770657.1, Response filed Sep. 30, 2019 to Communication Pursuant to Article 94(3) EPC dated May 20, 2019", 26 pgs.
"European Application Serial No. 16770657.1, Response filed Nov. 26, 2018 to Office Action dated May 14, 2018", 17 pgs.
"European Application Serial No. 17157909.7, Extended European Search Report dated Jul. 17, 2018", 7 pgs.
"European Application Serial No. 17157909.7, Response Filed Feb. 15, 2019 to Extended European Search Report dated Jul. 17, 2018", 37 pgs.
"European Application Serial No. 17163432.2, Extended European Search Report dated May 14, 2018", 6 pgs.
"European Application Serial No. 17163440.5, Extended European Search Report dated Jan. 3, 2019", 16 pgs.
"European Application Serial No. 17163440.5, Partial European Search Report dated Jul. 23, 2018", 15 pgs.
"European Application Serial No. 17163440.5, Response filed Jul. 22, 2019 to Extended European Search Report dated Jan. 3, 2019", 14 pgs.
"European Application Serial No. 17168095.2, Extended European Search Report dated Jun. 8, 2018", 8 pgs.
"European Application Serial No. 17168095.2, Response Filed Jan. 17, 2019 Extended European Search Report dated Jun. 8, 2018", 29 pgs.
"European Application Serial No. 17168308.9, Extended European Search Report dated Jun. 13, 2018", 8 pgs.
"European Application Serial No. 17168308.9, Response Filed Jan. 17, 2019 to Extended European Search Report dated Jun. 13, 2018", 24 pgs.

(56) References Cited

OTHER PUBLICATIONS

"European Application Serial No. 18206326.3, Extended European Search Report dated Apr. 15, 2019", 10 pgs.
"European Application Serial No. 18206326.3, Response filed Nov. 22, 2019 to Extended European Search Report dated Apr. 15, 2019", 15 pgs.
"European Application Serial No. 19171990.5, Extended European Search Report dated Oct. 16, 2019", 8 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"Gender Solutions Natural-Knee Flex System", Zimmer, Inc., (2007, 2009), 6 pgs.
"Indian Application Serial No. 1544/DELNP/2013, Office Action dated May 21, 2019", (W/English Translation), 10 pgs.
"Indian Application Serial No. 1544/DELNP/2013, Response filed Nov. 18, 2019 to Office Action dated May 21, 2019", w/ English claims, 34 pgs.
"Indian Application Serial No. 1545/DELNP/2013, Office Action dated Dec. 9, 2019", (with English translation), 8 pages.
"International Application Serial No. PCT/US2011/045077, International Preliminary Report on Patentability dated Jul. 5, 2012", 23 pgs.
"International Application Serial No. PCT/US2011/045077, International Search Report and Written Opinion dated Jan. 9, 2012", 15 pgs.
"International Application Serial No. PCT/US2011/045078, International Preliminary Report on Patentability dated Feb. 7, 2013", 11 pgs.
"International Application Serial No. PCT/US2011/045078, International Search Report and Written Opinion dated Jan. 9, 2012", 14 pgs.
"International Application Serial No. PCT/US2011/045080, International Preliminary Report on Patentability dated Feb. 7, 2013", 13 pgs.
"International Application Serial No. PCT/US2011/045080, International Search Report dated Jan. 9, 2012", 7 pgs.
"International Application Serial No. PCT/US2011/045080, Written Opinion dated Jan. 9, 2012", 11 pgs.
"International Application Serial No. PCT/US2011/045082, International Preliminary Report on Patentability dated Feb. 7, 2013", 11 pgs.
"International Application Serial No. PCT/US2011/045082, International Search Report dated Jan. 9, 2012", 5 pgs.
"International Application Serial No. PCT/US2011/045082, Written Opinion dated Jan. 9, 2012", 10 pgs.
"International Application Serial No. PCT/US2011/045083, International Preliminary Report on Patentability dated Feb. 7, 2013", 8 pgs.
"International Application Serial No. PCT/US2011/045083, International Search Report dated Dec. 7, 2011", 2 pgs.
"International Application Serial No. PCT/US2011/045083, Written Opinion dated Dec. 7, 2011", 6 pgs.
"International Application Serial No. PCT/US2011/051021, International Preliminary Report on Patentability dated Mar. 21, 2013", 8 pgs.
"International Application Serial No. PCT/US2011/051021, International Search Report dated Nov. 23, 2011", 12 pgs.
"International Application Serial No. PCT/US2011/051021, Written Opinion dated Nov. 23, 2011", 7 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012", 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2012/035679, International Preliminary Report on Patentability dated May 30, 2014", 8 pgs.
"International Application Serial No. PCT/US2012/035679, International Search Report dated Jun. 8, 2012", 4 pgs.
"International Application Serial No. PCT/US2012/035679, Written Opinion dated Jun. 8, 2012", 7 pgs.
"International Application Serial No. PCT/US2012/035680, International Preliminary Report on Patentability dated May 30, 2014", 13 pgs.
"International Application Serial No. PCT/US2012/035680, Search Report dated Oct. 9, 2012", 7 pgs.
"International Application Serial No. PCT/US2012/035680, Written Opinion dated Oct. 9, 2012", 11 pgs.
"International Application Serial No. PCT/US2012/035683, International Preliminary Report on Patentability dated May 30, 2014", 9 pgs.
"International Application Serial No. PCT/US2012/035683, International Search Report and Written Opinion dated Jun. 5, 2012", 12 pgs.
"International Application Serial No. PCT/US2012/035684, International Preliminary Report on Patentability dated May 30, 2014", 14 pgs.
"International Application Serial No. PCT/US2012/035684, International Search Report dated Aug. 8, 2012", 9 pgs.
"International Application Serial No. PCT/US2012/035684, Written Opinion dated Jun. 8, 2012", 12 pgs.
"International Application Serial No. PCT/US2012/052132, International Preliminary Report on Patentability dated Jun. 5, 2014", 12 pgs.
"International Application Serial No. PCT/US2012/052132, International Search Report dated Jan. 10, 2013", 5 pgs.
"International Application Serial No. PCT/US2012/052132, Invitation to Pay Additional Fees and Partial Search Report dated Nov. 15, 2012", 7 pgs.
"International Application Serial No. PCT/US2012/052132, Written Opinion dated Jan. 10, 2013", 10 pgs.
"International Application Serial No. PCT/US2012/052340, International Preliminary Report on Patentability dated Aug. 14, 2014", 8 pgs.
"International Application Serial No. PCT/US2012/052340, Search Report dated Oct. 12, 2012", 4 pgs.
"International Application Serial No. PCT/US2012/052340, Written Opinion dated Oct. 12, 2012", 6 pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.
"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.
"International Application Serial No. PCT/US2016/052163, International Preliminary Report on Patentability dated Apr. 5, 2018", 10 pgs.
"International Application Serial No. PCT/US2016/052163, International Search Report dated Jan. 20, 2017", 7 pgs.
"International Application Serial No. PCT/US2016/052163, Invitation to Pay Add'l Fees and Partial Search Report dated Nov. 7, 2016", 7 pgs.

(56) References Cited

OTHER PUBLICATIONS

"International Application Serial No. PCT/US2016/052163, Written Opinion dated Jan. 20, 2017", 8 pgs.
"International Application Serial No. PCT/US2018/021571, International Preliminary Report on Patentability dated Sep. 19, 2019", 8 pgs.
"International Application Serial No. PCT/US2018/021571, International Search Report dated Jun. 7, 2018", 6 pgs.
"International Application Serial No. PCT/US2018/021571, Written Opinion dated Jun. 7, 2018", 6 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995,1997,1998), 36 pgs.
"Japanese Application Serial No. 2015-162707, Office Action dated Jun. 28, 2016", (W/English Translation), 8 pgs.
"Japanese Application Serial No. 2013-521854, Notice of Reason for Rejection dated Sep. 16, 2014", (W/ English Translation), 6 pgs.
"Japanese Application Serial No. 2013-521854, Response filed Dec. 16, 2014 to Notice of Reason for Rejection dated Sep. 16, 2014", W/ English Claims, 11 pgs.
"Japanese Application Serial No. 2013-521855, Amendment filed Jul. 22, 2014", (W/ English Translation), 20 pgs.
"Japanese Application Serial No. 2013-521855, Office Action dated Mar. 24, 2015", W/ English Translation, 8 pgs.
"Japanese Application Serial No. 2013-521856, Notice of Allowance dated Jan. 5, 2016", w/English Translation, 6 pgs.
"Japanese Application Serial No. 2013-521856, Office Action dated Sep. 1, 2015", (W/ English Translation), 5 pgs.
"Japanese Application Serial No. 2013-521856, Response filed Dec. 1, 2015 to Office Action dated Sep. 1, 2015", w/English Translation, 9 pgs.
"Japanese Application Serial No. 2013-521857, Notice of Allowance dated Feb. 9, 2016", w/English Translation, 6 pgs.
"Japanese Application Serial No. 2013-521857, Notice of Reasons for Rejection dated Aug. 18, 2015", (W/ English Translation), 6 pgs.
"Japanese Application Serial No. 2013-521857, Preliminary Amendment filed May 18, 2014", (W/ English translation of claims), 9 pgs.
"Japanese Application Serial No. 2013-521857, Response filed Jan. 25, 2016 to Notice of Reasons for Rejection dated Aug. 18, 2015", (W/ English Translation), 17 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", (W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection dated Jan. 5, 2016", (W/ English Translation of Claims), 11 pgs.
"Japanese Application Serial No. 2014-121515, Response filed Aug. 20, 2015 to Office Action dated Jun. 2, 2015", (W/ English Translation of Claims), 6 pgs.
"Japanese Application Serial No. 2014-542297, Office Action dated May 31, 2016", (W/ English Translation of Claims), 6 pgs.
"Japanese Application Serial No. 2014-542297, Office Action dated Jun. 30, 2015", (W/ English Translation), 10 pgs.
"Japanese Application Serial No. 2014-542297, Office Action dated Nov. 24, 2015", (W/ English Translation), 10 pgs.
"Japanese Application Serial No. 2014-542297, Response filed Feb. 23, 2016 to Office Action dated Nov. 24, 2015", (W/ English Translation of Claims), 15 pgs.
"Japanese Application Serial No. 2014-542297, Response filed Jun. 8, 2016 to Office Action dated May 31, 2016", (W/ English Translation of Claims), 14 pgs.
"Japanese Application Serial No. 2014-542297, Response filed Sep. 28, 2015 to Office Action dated Jun. 30, 2015", (W/ English Translation of Claims), 16 pgs.
"Japanese Application Serial No. 2014-542301, Office Action dated May 12, 2015", (W/ English Translation), 6 pgs.
"Japanese Application Serial No. 2014-542301, Response filed Aug. 10, 2015 to Office Action dated May 12, 2015", (W/ English translation of claims), 21 pgs.
"Japanese Application Serial No. 2014-554709, Office Action dated Jul. 5, 2016", (W/ English Translation), 6 pgs.
"Japanese Application Serial No. 2014-554709, Preliminary Amendment filed Jul. 29, 2015", (W/ English translation of claims), 8 pgs.
"Japanese Application Serial No. 2014-554709, Response filed Dec. 19, 2016 to Office Action dated Jul. 5, 2016", (W/ English Translation of Claims), 11 pgs.
"Japanese Application Serial No. 2015-162707, Office Action dated Nov. 29, 2016", (W/ English Translation), 3 pgs.
"Japanese Application Serial No. 2015-162707, Response filed Jan. 26, 2017 to Office Action dated Nov. 27, 2016", (W/ English Translation), 16 pgs.
"Japanese Application Serial No. 2015-199496, Office Action dated Sep. 6, 2016", (W/ English Translation), 5 pgs.
"Japanese Application Serial No. 2015-199496, Response filed Dec. 5, 2016 to Office Action dated Sep. 6, 2016", (W/ English Translation of Claims), 9 pgs.
"Japanese Application Serial No. 2015-503563, Office Action dated Dec. 20, 2016", (W/ English Translation), 10 pgs.
"Japanese Application Serial No. 2015-503563, Response Filed Mar. 13, 2017 to Office Action dated Dec. 20, 2016", (W/ English Translation), 9 pgs.
"Japanese Application Serial No. 2016-145390, Office Action dated Apr. 25, 2017", (W/ English Translation), 5 pgs.
"Japanese Application Serial No. 2016-145390, Response filed Jul. 3, 2017 to Office Action dated Apr. 25, 2017", (W/ English Translation of Claims), 16 pgs.
"Japanese Application Serial No. 2017-161246, Office Action dated May 15, 2018", (W/ English Translation), 6 pgs.
"Journey II XR, Bi-Cruciate Retaining Knee System", Smith & Nephew, Surgical Technique, (2015), 40 pgs.
"Legacy Implant Options", Nexgen Complete Knee Solution, (2002), 8 pgs.
"LPS-Flex Fixed Bearing Knee: Surgical Technique", Zimmer, Inc., (2004, 2007, 2008), 16 pgs.
"Mexican Application Serial No. MX/a/2013/000988, Office Action dated Mar. 18, 2015", w/English Claims, 17 pgs.
"Mexican Application Serial No. MX/a/2013/000988, Response filed Jun. 1, 2015 to Office Action dated Mar. 18, 2015", (W/ English Translation), 12 pgs.
"Mexican Application Serial No. MX/A/2013/000988. Office Action dated Jun. 5, 2015", w/summary in English, 6 pgs.
"Mexican Application Serial No. MX/A/2013/000990, Final Office Action dated Feb. 4, 2016", w/summary in English, 4 pgs.
"Mexican Application Serial No. MX/A/2013/000990, Office Action dated Feb. 19, 2015", (W/English Translation), 4 pgs.
"Mexican Application Serial No. MX/A/2013/000990, Response filed Apr. 29, 2015 to Office Action dated Feb. 19, 2015", W/ English Claims, 18 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.
"Natural-Knee II Primary System Surgical Technique", Zimmer, Inc., (2005), 48 pgs.

(56) References Cited

OTHER PUBLICATIONS

"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.
"Nexgen Complete Knee Solution", Extramedullary/Intramedullary Tibial Resector: Surgical Technique, Zimmer, Inc. 97-5997-02 Rev 1, (2000), 26 pgs.
"Nexgen Complete Knee Solution for the Legacy Knee LPS-Flex Fixed Bearing Knee", Zimmer Surgical Technique, 97-5964-102-00, (2004, 2007), 12 pgs.
"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"NexGen Trabecular Metal Modular Plates", Zimmer Inc., (2007), 19 pgs.
"Persona "Medial Congruent Articular Surface" System Overview", Zimmer, Inc., (2015), 6 pgs.
"Persona "The Personalized Knee System"", Medial Congruent Sales Training, Zimmer, Inc., (Jul. 2015), 53 pgs.
"Persona "The Personalized Knee System" Medial Congruent Advanced Bearings", Zimmer, Inc., (2015), 2 pgs.
"Persona "The Personalized Knee System" Medial Congruent Articular Surface Design Rationale", Zimmer, Inc., (2015), 20 pgs.
"Persona "The Personalized Knee System" Persona Medial Congruent", Mar. 24-28, 2015 at the American Academy of Orthopaedic Surgeons (AAOS) Annual Meeting., (Mar. 2015), 1 pg.
"Persona "The Personalized Knee System" Surgical Technique", Zimmer, Inc., (2015), 72 pgs.
"Persona Medial Congruent Articular Surface", Sales Training, Zimmer Biomet, (Jan. 2016), 71 pgs.
"PFC Sigma Knee System with Rotating Platform Technical/ Monograph", Depuy PFC Sigma RP, 0611-29-050 (Rev. 3), (1999), 70 pgs.
"Primary/Revision Surgical Technique for NexGen Rotating Hinge Knee (RHK)", Zimmer, Inc. Nexgen Complete Knee Solution, 97-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.
"Russian Application Serial No. 2013106942, Office Action dated Apr. 16, 2015", W/ English Translation, 5 pgs.
"Russian Application Serial No. 2013106942, Response filed Jul. 15, 2015 Office Action dated Apr. 16, 2015", (W/ English translation of claims), 146 pgs.
"Russian Application Serial No. 2013106943, Office Action dated Jul. 1, 2015", (W/ English Translation), 6 pgs.
"Russian Application Serial No. 2013106943, Office Action dated Dec. 28, 2015", w/ partial English Translation, 6 pgs.
"Russian Application Serial No. 2013106943, Response filed Apr. 28, 2016 to Office Action dated Dec. 28, 2015", (W/ English translation of claims), 19 pgs.
"Russian Application Serial No. 2013106943, Response filed Oct. 30, 2015 to Office Action dated Jul. 1, 2015", (W/ English translation of claims), 21 pgs.
"South African Application Serial No. 2013/01327, Amendment filed Apr. 24, 2014", W/ English Translation, 4 pgs.
"South African Application Serial No. 2013/01328, Amendment filed Apr. 24, 2014", W/ English Translation, 4 pgs.
"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.
"Surgical Technique for the CR-Flex Fixed Bearing Knee", NexGen Complete Knee Solution, Zimmer, Inc., (2003), 22 pgs.
"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.
"Surgical Technique for the Legacy Posterior Stabilized Knees", Zimmer, Inc. Nexgen Complete Knee Solution, 97-5996-02, (2002), 43 pgs.
"Surgical Technique—Nexgen Complete Knee Solution for the Legacy Knee LPS-Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Tibial Baseplate: Pocket Guide (United States Version)", Zimmer, Inc.,, (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
"Turkish Application Serial No. 11808493.8, Working Requirements dated Feb. 17, 2020", 3 pgs.
"Turkish Application Serial No. 12718882.9, Working Requirements dated Feb. 13, 2020", 3 pgs.
"Vanguard® ID Total Knee, Surgical Technique", Zimmer Biomet; 0682.1-GLBL-en-REV0317, (2017), 36 pgs.
"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.
"Zimmer NexGen CR-Flex and LPS-Flex Knees Surgical Technique with posterior Referencing Instrumentation.", Zimmer Inc., (2010, 2011), 48 pgs.
"Zimmer NexGen LCCK Surgical Technique for use with LCCK 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure-97-5950-001-00 7.5mm, (2005, 2006), 8 pgs.
"Zimmer NexGen MIS Tibial Component Cemented Surgical Technique", Zimmer, Inc, #97-5950-002-00 Rev.1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.
"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Annayappa, Ramesh, "Tibial Prosthesis", U.S. Appl. No. 13/189,328, filed Jul. 22, 2011, 82 pgs.
Annayappa, Ramesh, et al., "Tibial Prosthesis", U.S. Appl. No. 13/189,324, filed Jul. 22, 2011, 50 pgs.
Bellemans, Johan, et al., "Is Neutral Mechanical Alignment Normal for All Patients?", Clinical Orthopaedics and Related Research; DOI 10.1007/s11999-011-1936-5, (Jun. 9, 2011), 9 pgs.
Ding, M., et al., "Age-related variations in the microstructure of human tibial cancellous bone", Journal of Orthopaedic Research, 20(3), (2002), 615-621.
Ding, M., et al., "Changes in the three-dimensional microstructure of human tibial cancellous bone in early osteoarthritis", Journal of Bone & Joint Surgery (British), 85-B(6), (Aug. 2003), 906-912.

(56) References Cited

OTHER PUBLICATIONS

Doyle, et al., "Comparative Analysis of Human Trabecular Bone and Polyurethane Foam", Purdue University., 1 pg.
Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Freeman, M.A.R., et al., "The Movement of the Knee Studied by Magnetic Resonance Imaging", Advanced Bearings—Clinical Orthopedics & Related Research 2003, (2003), 1 pg.
Hofmann, Aaron A, et al., "Posterior Stabilization in Total Knee Arthroplasty with Use of an Ultracongruent Polyethylene", The Journal of Arthroplasty vol. 15, No. 5, (2000), 576-583.
Hutt, Jonathan, et al., "Functional joint line obliquity after kinematic total knee arthroplasty", International Orthopaedics; DOI 10.1007/s00264-015-2733-7, (Mar. 21, 2015), 6 pgs.
Hvid, Ivan, et al., "Trabecular bone Strength Patterns at the Proximal Tibial Epiphysis", Journal of Orthopaedic Research, vol. 3, No. 4, (1985), 464-472.
Klostermann, et al., "Distribution of bone mineral density with age and gender in the proximal tibia", Clinical Biomechanics 19, 376-376.
Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.
Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.
Parisi, Raymond C, "Motion Facilitating Tibial Components for a Knee Prosthesis", U.S. Appl. No. 13/229,103, filed Sep. 9, 2011, 46 pgs.
Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.
Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.
Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.
Stilling, et al., "Superior fixation of pegged trabecular metal over screw-fixed pegged porous titanium fiber mesh", Acta Orthopaedica., (2011), 177-186.
Victor, Jan M. K., et al., "Constitutional Varus Does Not Affect Joint Line Orientation in the Coronal Plane", Joint Line Orientation in the Coronal Plane; 472; DOI 10.1007/s11999-013-2898-6, (Jun. 4, 2013), pp. 98-104.
Wentorf, Mary S. S, "Asymmetric Tibial Components for a Knee Prosthesis", U.S. Appl. No. 13/189,338, filed Jul. 22, 2011, 58 pgs.
Wentorf, Mary S. S, "Asymmetric Tibial Components for a Knee Prosthesis", U.S. Appl. No. 13/189,339, filed Jul. 22, 2011, 52 pgs.
Wentorf, Mary S. S, "Asymmetric Tibial Components for a Knee Prosthesis", U.S. Appl. No. 13/189,336, filed Jul. 22, 2011, 60 pgs.
U.S. Appl. No. 13/087,610 U.S. Pat. No. 8,603,101, filed Apr. 15, 2011, Provisional Tibial Prosthesis System.
U.S. Appl. No. 14/063,032 U.S. Pat. No. 9,011,459, filed Oct. 25, 2013, Provisional Tibial Prosthesis System.
U.S. Appl. No. 14/660,217 U.S. Pat. No. 9,427,337, filed Mar. 17, 2015, Provisional Tibial Prosthesis System.
U.S. Appl. No. 15/211,812 U.S. Pat. No. 9,763,807, filed Jul. 15, 2016, Provisional Tibial Prosthesis System.
U.S. Appl. No. 15/703,698 U.S. Pat. No. 10,188,530, filed Sep. 13, 2017, Provisional Tibial Prosthesis System.
U.S. Appl. No. 13/189,324 U.S. Pat. No. 8,764,840, filed Jul. 22, 2011, Tibial Prosthesis.
U.S. Appl. No. 14/284,144 U.S. Pat. No. 9,283,082, filed May 21, 2014, Methods Related to Seating of Bearing Component on Tibial Tray.
U.S. Appl. No. 15/003,091 U.S. Pat. No. 9,918,844, filed Jan. 21, 2016, Tibial Prosthesis With a Fixed Bearing Componet.
U.S. Appl. No. 14/034,937 U.S. Pat. No. 9,861,490, filed Sep. 24, 2013, Asymmetric Tibial Components for a Knee Prosthesis.
U.S. Appl. No. 13/189,336 U.S. Pat. No. 8,613,775, filed Jul. 22, 2011, Asymmetric Tibial Components for a Knee Prosthesis.
U.S. Appl. No. 15/827,654 U.S. Pat. No. 10,470,889, filed Nov. 30, 2017, Asymmetric Tibial Components for a Knee Prosthesis.
U.S. Appl. No. 16/596,194, filed Oct. 8, 2019, Asymmetric Tibial Components for a Knee Prosthesis.
U.S. Appl. No. 13/189,328 U.S. Pat. No. 8,628,580, filed Jul. 22, 2011, Tibial Prosthesis.
U.S. Appl. No. 14/063,593 U.S. Pat. No. 9,763,794, filed Oct. 25, 2013, Tibial Prosthesis.
U.S. Appl. No. 15/703,678 U.S. Pat. No. 10,543,099, filed Sep. 13, 2017, Tibial Prosthesis.
U.S. Appl. No. 16/715,092, filed Dec. 16, 2019, Tibial Prosthesis.
U.S. Appl. No. 13/229,103 U.S. Pat. No. 8,591,594, filed Sep. 9, 2011, Motion Facilitating Tibia Components for a Knee Prosthesis.
U.S. Appl. No. 14/034,963 U.S. Pat. No. 9,314,343, filed Sep. 24, 2013, Motion Facilitating Tibia Components for a Knee Prosthesis.
U.S. Appl. No. 14/791,952 U.S. Pat. No. 9,763,795, filed Jul. 6, 2015, Motion Facilitating Tibia Components for a Knee Prosthesis.
U.S. Appl. No. 15/703,692 U.S. Pat. No. 10,413,415, filed Sep. 13, 2017, Motion Facilitating Tibia Components for a Knee Prosthesis.
U.S. Appl. No. 16/530,423, filed Aug. 2, 2019, Motion Facilitating Tibia Components for a Knee Prosthesis.
U.S. Appl. No. 13/189,338 U.S. Pat. No. 8,568,486, filed Jul. 22, 2011, Asymmetric Tibial Components for a Knee Prosthesis.
U.S. Appl. No. 14/034,944 U.S. Pat. No. 9,192,480, filed Sep. 24, 2013, Asymmetric Tibial Components for a Knee Prosthesis.
U.S. Appl. No. 13/189,339 U.S. Pat. No. 8,574,304, filed Jul. 22, 2011, Asymmetric Tibial Components for a Knee Prosthesis.
U.S. Appl. No. 14/034,954 U.S. Pat. No. 9,295,557, filed Sep. 24, 2013, Asymmetric Tibial Components for a Knee Prosthesis.
U.S. Appl. No. 13/593,339 U.S. Pat. No. 8,758,444, filed Aug. 23, 2013, Tibial Baseplate With Asymmetric Placement of Fixation Structures.
U.S. Appl. No. 14/278,805 U.S. Pat. No. 9,308,096, filed May 15, 2014, Tibial Baseplate With Asymmetric Placement of Fixation Structures.
U.S. Appl. No. 15/045,799 U.S. Pat. No. 9,707,089, filed Feb. 17, 2016, Tibial Baseplate With Asymmetric Placement of Fixation Structures.
U.S. Appl. No. 15/616,561 U.S. Pat. No. 10,265,181, filed Jun. 7, 2017, Tibial Baseplate With Asymmetric Placement of Fixation Structures.
U.S. Appl. No. 13/459,037 U.S. Pat. No. 8,858,643, filed Apr. 27, 2012, Tibial Bearing Component for a Knee Prosthesis With Improved Articular Characteristics.
U.S. Appl. No. 14/490,153 U.S. Pat. No. 9,204,970, filed Sep. 18, 2014, Tibial Bearing Component for a Knee Prosthesis With Improved Articular Characteristics.
U.S. Appl. No. 14/926,281 U.S. Pat. No. 9,925,050, filed Oct. 29, 2011, Tibial Bearing Component for a Knee Prosthesis With Improved Articular Characteristics.
U.S. Appl. No. 13/594,543 U.S. Pat. No. 9,381,090, filed Aug. 24, 2012, Asymmetric Tibial Components for a Knee Prosthesis.
U.S. Appl. No. 15/177,734 U.S. Pat. No. 9,763,796, filed Jun. 9, 2016, Asymmetric Tibial Components for a Knee Prosthesis.
U.S. Appl. No. 15/703,713 U.S. Pat. No. 10,195,041, filed Sep. 13, 2017, Asymmetric Tibial Components for a Knee Prosthesis.
U.S. Appl. No. 13/459,041 U.S. Pat. No. 9,072,607, filed Apr. 27, 2012, Tibial Bearing Component for a Knee Prosthesis With Improved Articular Characteristics.

(56) References Cited

OTHER PUBLICATIONS

U.S. Appl. No. 14/740,690 U.S. Pat. No. 9,788,954, filed Jun. 16, 2015, Tibial Bearing Component for a Knee Prosthesis With Improved Articular Characteristics.
U.S. Appl. No. 15/720,866, filed Sep. 29, 2017, Tibial Bearing Component for a Knee Prosthesis With Improved Articular Characteristics.
U.S. Appl. No. 13/459,048 U.S. Pat. No. 8,690,954, filed Apr. 27, 2012, Tibial Bearing Component for a Knee Prosthesis With Improved Articular Characteristics.
U.S. Appl. No. 14/181,033 U.S. Pat. No. 9,186,255, filed Feb. 14, 2014, Tibial Bearing Component for a Knee Prosthesis With Improved Articular Characteristics.
U.S. Appl. No. 14/918,721 U.S. Pat. No. 9,655,728, filed Oct. 21, 2015, Tibial Bearing Component for a Knee Prosthesis With Improved Articular Characteristics.
U.S. Appl. No. 13/459,056 U.S. Pat. No. 8,764,838, filed Apr. 27, 2012, Tibial Bearing Component for a Knee Prosthesis With Biproved Articular Characteristics.
U.S. Appl. No. 14/284,028 U.S. Pat. No. 9,295,558, filed May 21, 2014, Tibial Bearing Component for a Knee Prosthesis With Improved Articular Characteristics.
U.S. Appl. No. 15/062,262 U.S. Pat. No. 9,655,729, filed Mar. 7, 2016, Tibial Bearing Component for a Knee Prosthesis With Improved Articular Characteristics.
U.S. Appl. No. 14/471,440 U.S. Pat. No. 9,925,052, filed Aug. 28, 2014, Method for Optimizing Implant Designs.
U.S. Appl. No. 15/890,735 U.S. Pat. No. 10,575,956, filed Feb. 7, 2018, Method for Optimizing Implant Designs.
U.S. Appl. No. 16/743,746, filed Jan. 15, 2020, Method for Optimizing Implant Designs.
U.S. Appl. No. 15/267,793 U.S. Pat. No. 10,278,827, filed Sep. 16, 2016, Prosthesis System Including Tibial Bearing Component.
U.S. Appl. No. 16/352,287, filed Mar. 13, 2019, Prosthesis System Including Tibial Bearing Component.
U.S. Appl. No. 15/915,886, filed Mar. 8, 2018, Tibial Prosthesis With Tibial Bearing Component Securing Feature.
U.S. Appl. No. 16/179,201, filed Nov. 2, 2018, Implants for Adding Joint Inclination to a Knee Arthroplasty.
U.S. Appl. No. 16/389,381, filed Apr. 19, 2019, Posterior Stabilized Prosthesis System.
"U.S. Appl. No. 16/179,201, Supplemental Notice of Allowability dated Aug. 2, 2022", 2 pgs.
"U.S. Appl. No. 16/530,423, Notice of Allowance dated Jun. 14, 2022", 6 pgs.
"U.S. Appl. No. 16/530,423, Response filed Jun. 1, 2022 to Non Final Office Action dated Mar. 3, 2022", 14 pgs.
"U.S. Appl. No. 17/717,898, Preliminary Amendment filed Apr. 29, 2022", 7 pgs.
"U.S. Appl. No. 17/866,151, Preliminary Amendment filed Aug. 3, 2022", 6 pgs.
"European Application Serial No. 21177256.1, Extended European Search Report dated May 17, 2022", 9 pgs.
"Japanese Application Serial No. 2021-097369, Notification of Reasons for Rejection dated Jun. 14, 2022", w/ English Translation, 11 pgs.

\* cited by examiner

TIBIAL PROSTHESIS WITH TIBIAL BEARING COMPONENT SECURING FEATURE

CLAIM OF PRIORITY

This application is a continuation of U.S. patent application Ser. No. 15/915,886, filed Mar. 8, 2018, which claims the benefit of U.S. Provisional Patent Application Ser. No. 62/469,924, filed on Mar. 10, 2017, the benefit of priority of each of which is claimed hereby, and each of which is incorporated by reference herein in its entirety.

FIELD

The present subject matter relates to orthopedic prostheses and, more particularly, to prostheses, systems and methods used in knee arthroplasties including revision knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

This disclosure pertains generally to tibial prostheses, systems, and methods for a knee arthroplasty including a revision knee arthroplasty. The present inventors have recognized, among other things, that a degree of micro-motion experienced by a tibial bearing component relative to a tibial baseplate can be reduced by providing an additional lockdown feature(s). Reduction of micro-motion can provide better overall durability for the tibial beating component when assembled with the tibial baseplate. Furthermore, present inventors have recognized that with additional lockdown features, a greater rigidity and torsional strength can be provided to the tibial bearing component. As such, metal reinforcement need not be provided to a spine of the tibial bearing component. Thus, the weight of the tibial bearing component can be reduced.

As used herein, "micro-motion" refers to the small motions that may exist between prosthesis components, such as between the tibial baseplate and the tibial bearing component, respectively, upon application of force. Such small motions may occur as a result of material deformation in one or both of the interacting components, or may result from slight spaces or clearances therebetween, for example. Micro-motion is distinguished from "mobile bearing" applications, which experience relatively larger motions as the tibial bearing component articulates with respect to the tibial baseplate (such as by sliding or rotating) along a desired motion path.

As used herein, a "fixed bearing" tibial prosthesis is a prosthesis in which the tibial bearing component is seated atop the tibial baseplate in a final, locked, and secured position. In this secured position, lift-off of the tibial bearing component from the tibial baseplate as well as transverse movement of the tibial bearing component relative to the tibial baseplate is prevented during natural articulation of the knee. Some micro-motion may exist between the tibial bearing component and tibial baseplate in a fixed bearing prosthesis.

To further illustrate the apparatuses and systems disclosed herein, the following non-limiting examples are provided:

Example 1 is a tibial prosthesis for a knee arthroplasty that can optionally comprise: a tibial bearing component having medial and lateral proximal articular surfaces and an opposing distal surface, wherein the tibial bearing component defines at least one recess therein with the recess having an opening at a periphery of the tibial bearing component; a tibial baseplate coupled to the tibial beating component on a proximal surface thereof and having a distal surface configured to be disposed on a resected proximal surface of a tibia; an insert configured to be disposed within the recess and engage the tibial baseplate and the tibial bearing component; and a fastener retaining the insert to the tibial baseplate.

In Example 2, the subject matter of Example 1 can optionally include wherein the tibial bearing component comprises a posterior-stabilized tibial bearing component with a spine disposed between the medial and lateral proximal articular surfaces.

in Example 3, the subject matter of any one or more of Examples 1-2 can optionally include wherein the insert comprises: a body having an aperture defined thereby, the aperture receives a head of the fastener; a first foot connected to the body and extending distal therefrom, the first foot having a first side surface engaging the tibial baseplate; and a second foot connected to the body and extending distal therefrom, the second foot spaced from the first foot and having a second side surface engaging the tibial baseplate.

In Example 4, the subject matter of Example 3 can optionally include wherein the insert further comprises a tab extending proximally from the body, the tab engaging the tibial bearing component to retain the insert within the tibial bearing component.

In Example 5, the subject matter of any one or more of Examples 3-4 can optionally include wherein the body includes a first wing that extends lateral of the first foot and a second wing that extends medial of the second foot.

in Example 6, the subject matter of any one or more of Examples 3-5 can optionally include wherein the head of the fastener and the aperture share a similar curvature such the fastener is self-centering within the insert.

In Example 7, the subject matter of any one or more of Examples 1-6 can optionally include wherein the opening is at an anterior portion of the periphery of the tibial bearing component and the insert is disposed in the recess such that substantially an entirety of the insert is disposed anterior of the fastener.

In Example 8, the subject matter of any one or more of Examples 1-7 can optionally include wherein the tibial baseplate includes a rail extending from the proximal surface along a periphery thereof, wherein the rail has a gap in a region of the recess, and wherein with the insert disposed in the recess, at least a portion thereof extends into the gap and engages the rail to limit micro-motion of the tibial bearing component.

In Example 9, the subject matter of any one or more of Examples 1-8 can optionally include a second aperture formed in the tibial bearing component and extending from between the medial and lateral proximal articular surfaces to communicate with the recess, wherein the second aperture is configured to receive at least a portion of the fastener, and wherein the second aperture is angled relative to a proximal-distal axis of the tibial bearing component such that second aperture extends both proximal-distal and anterior-posterior.

Example 10 is a system for use in a knee arthroplasty can optionally comprise: a tibial bearing component having medial and lateral proximal articular surfaces and an opposing distal surface, wherein the tibial bearing component defines at least one recess therein with the recess having an opening at a periphery of the tibial bearing component; a tibial baseplate configured to receive the tibial bearing component on a proximal surface thereof and having a distal surface configured to be disposed on a resected proximal surface of a tibia; an insert disposable through the opening and into the recess, the insert configure to engage the tibial baseplate and the tibial bearing component when the insert, the tibial baseplate and the tibial bearing component are assembled together; and a fastener insertable into the tibial bearing component and configured to retain the insert to the tibial baseplate.

In Example 11, the subject matter of Example 10 can optionally include wherein the tibial bearing component comprises a posterior-stabilized tibial bearing component with a spine disposed between the medial and lateral proximal articular surfaces, and wherein the fastener is insertable into an anterior portion of the spine.

In Example 12, the subject matter of any one or more of Examples 10-11 can optionally include wherein the insert comprises: a body having an aperture defined thereby, the aperture configured to receive a head of the fastener, a first foot extending generally distal from the body and having a first side surface engaging the tibial baseplate; and a second foot extending generally distal from the body and spaced from the first foot, the second foot having a second side surface engaging the tibial baseplate.

In Example 13, the subject matter of Example 12 can optionally include wherein the insert further comprises a tab extending proximally from the body and configured to engage the tibial bearing component to retain the insert within the tibial bearing component.

In Example 14, the subject matter of any one or more of Examples 12-13 can optionally include wherein the body includes a first wing that extends lateral of the first foot and a second wing that extends medial of the second foot.

In Example 15, the subject matter of any one or more of Examples 12-14 can optionally include wherein the head of the fastener and the aperture share a similar curvature such the fastener is self-centering within the insert.

In Example 16, the subject matter of any one or more of Examples 10-15 can optionally include wherein the opening is at an anterior portion of the periphery of the tibial bearing component and the insert is disposed in the recess when assembled such that substantially an entirety of the insert is disposed anterior of the fastener.

In Example 17, the subject matter of any one or more of Examples 10-16 can optionally include wherein the tibial baseplate includes a rail extending from the proximal surface along a periphery thereof, wherein the rail has a gap in a region of the recess and forms a part of the opening, and wherein with the insert disposed in the gap the insert is configured to engage the rail to limit micro-motion of the tibial bearing component.

In Example 18, the subject matter of any one or more of Examples 10-17 can optionally include a second aperture formed in the tibial bearing component and extending from the medial and lateral proximal articular surfaces to communicate with the recess, wherein the second aperture is configured to receive at least a portion of the fastener, and wherein the second aperture is angled relative to a proximal-distal axis of the tibial bearing component such that second aperture extends both proximal-distal and anterior-posterior.

Example 19 is a method of assembling a tibial prosthesis for a knee arthroplasty, the method can optionally comprise: passing an insert through a peripheral opening and into a recess formed in a tibial bearing component; engaging a portion of the insert with the tibial bearing component while having wings of the insert received in corresponding grooves that are part of the recess; engaging the tibial bearing component with a tibial baseplate; and fastening the insert to the tibial baseplate.

In Example 20, the subject matter of Example 19 can optionally include wherein fastening the insert to the tibial baseplate includes passing a fastener through a proximal surface region located between medial and lateral proximal articular surfaces of the tibial bearing component.

In Example 21, the subject matter of any one or more of Examples 19-20 can optionally include engaging a first foot of the insert with a first portion of a rail of the tibial baseplate and engaging a second foot of the insert with a second portion of the rail of the tibial baseplate.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates tibial prostheses, systems, and methods. The systems, for example, can include a tibial bearing component, a tibial baseplate, an insert and a fastener.

The present application relates a prosthesis assembly that can be used in a knee arthroplasty and/or as part of a later knee revision surgery. As described herein, the prosthesis assembly can include tibial prosthesis and a femoral prosthesis. This application focuses on aspects of the tibial prosthesis, which can include a tibial baseplate, a tibial bearing component, an insert and a fastener. As discussed previously, the tibial prosthesis can be configured to reduce micro-motion between the tibial bearing component and the tibial baseplate. This can improve the durability of the tibial prosthesis. Additional features and benefits of the various examples provided herein will be discussed and/or will be apparent to one of ordinary skill in the art.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior", Similarly, the term "lateral" refers to the opposite direction of "medial".

Figure 1A:
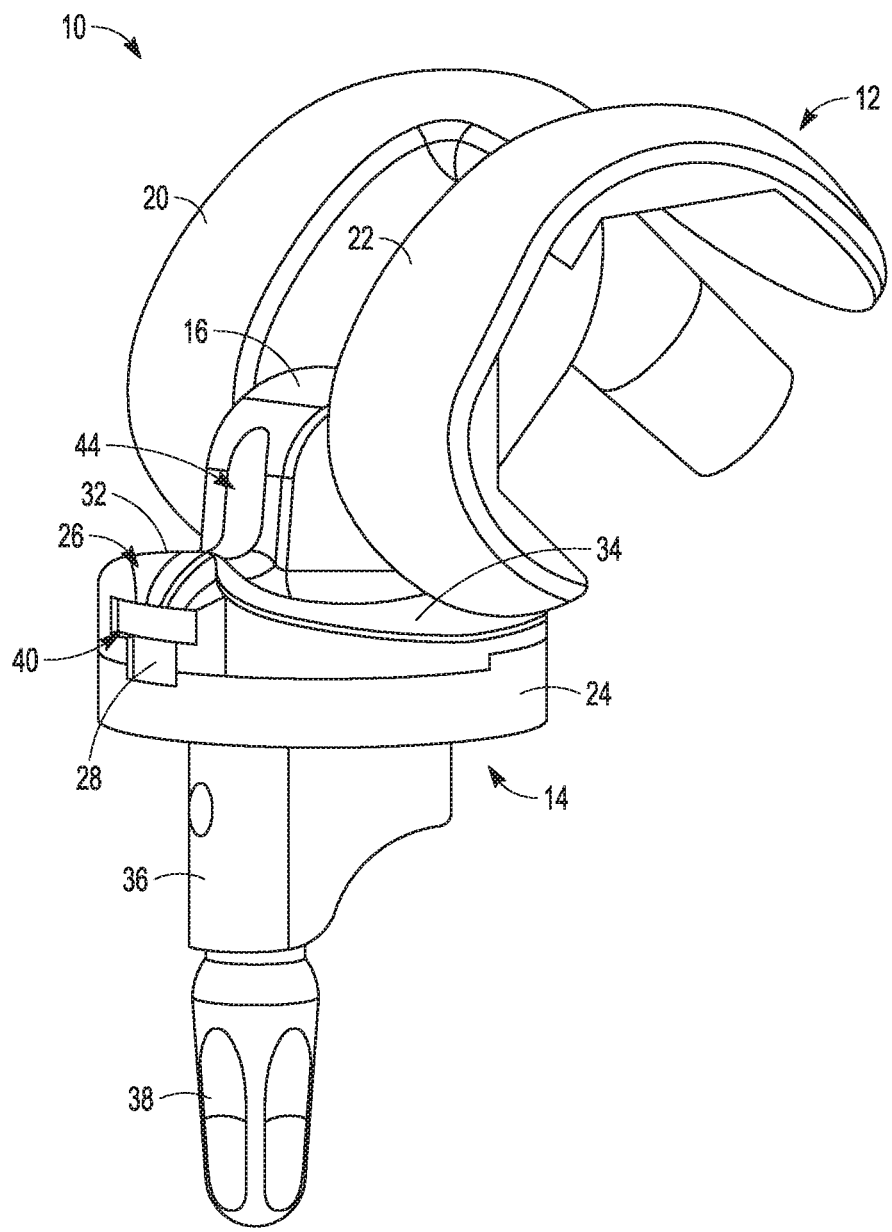
FIG. 1A shows a perspective view of a prosthesis assembly including a femoral component, tibial bearing component and tibial baseplate according to an example of the present application.
Figure 1B:
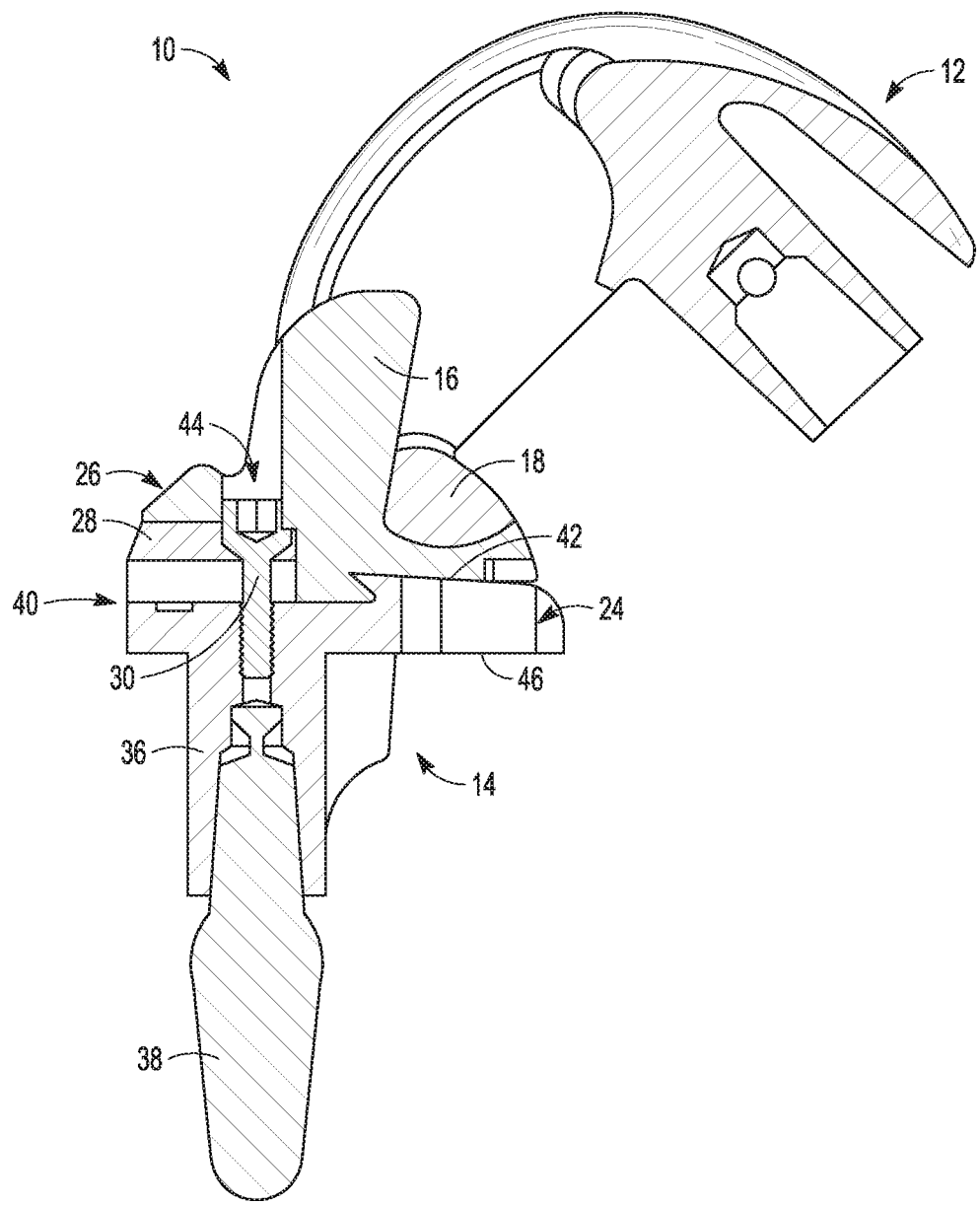
FIG. 1B show a cross-sectional view of the prosthesis assembly of FIG. 1A showing an insert and a fastener in addition to the aforementioned femoral component, tibial bearing component and tibial baseplate according to an example of the present application.

FIGS. 1A and 1B illustrate a prosthesis assembly 10 that can include a femoral prosthesis 12 and a tibial prosthesis 14. In the example of FIG. 1A, the prosthesis assembly 10 is shown in a perspective view with the femoral prosthesis 12 articulated relative to the tibial prosthesis 14 to 135° of flexion. FIG. 1B shows the prosthesis assembly 10 in a cross-sectional view along a sagittal plane. The sagittal plane extends along the anterior-posterior direction and the proximal-distal direction of the prosthesis assembly 10.

According to the examples provided herein, the prosthesis assembly 10 can comprise a posterior stabilized (PS) prosthesis. Thus, the tibial prosthesis can include a spine 16 and the femoral prosthesis 12 can include a cam 18 (FIG. 1B). The spine 16 and the cam 18 can designed to cooperate with one another to stabilize femoral prosthesis 12 with respect to tibial prosthesis 14 in lieu of a posterior cruciate ligament (PCL). However, other prosthesis designs are contemplated including a mid-level constraint (MLC) design, a cruciate retaining (CR) design, and an ultra-congruent (UC) design, for example. The CR and UC designs omit the spine 16 and cam 18, such that femoral prosthesis 12 defines an intercondylar space between medial and lateral condyles 20 and 22 (only one shown in FIG. 1B) that is entirely open and uninterrupted by the cam 18. CR tibial prostheses are generally used in surgical procedures which retain the PCL.

Turning to the components illustrated in FIG. 1A and/or FIG. 1B, the tibial prosthesis 14 can include a tibial bearing component 26, a tibial baseplate 24, an insert 28, and a fastener 30 (FIG. 1B). The tibial bearing component 26 can include the spine 16, a proximal medial articular surface 32 and a proximal lateral articular surface 34. The tibial baseplate 24 can include a keel 36. Additional components such as a stem 38 can be used with the prosthesis assembly 10 in some examples.

As shown in FIGS. 1A and 1B, the femoral prosthesis 12 can be disposed atop and can articulate relative to the tibial prosthesis 14. Such articulation can be between the medial and lateral condyles 20 and 22 and the proximal medial articular surface 32 and the proximal lateral articular surface 34, respectively. The proximal medial articular surface 32 and the proximal lateral articular surface 34 can be shaped (e.g., curved) to facilitate such articulation during knee joint flexion. The spine 16 of the tibial bearing component 26 can be centrally located between the proximal medial articular surface 32 and the proximal lateral articular surface 34 as shown in FIG. 1A. The spine 16 can be configured to engage with the cam 18 during flexion as shown in FIG. 1B. Such engagement provides additional stability that would otherwise be offered by ligaments such as the PCL.

The tibial bearing component 26 can be secured to the tibial baseplate 24 as shown in FIGS. 1A and 1B. Such securement can be facilitated by the use of rails, notches, bosses and other features that will be described subsequently. Additionally, as shown in FIG. 1B, the insert 28 and the fastener 30 can be used to further secure the tibial beating component 26 to the tibial baseplate 24 as will be described subsequently.

As shown in FIG. 1B, the insert 28 can be disposed within a recess 40 of the tibial bearing component 26 atop a proximal surface 42 of the tibial baseplate 24 when assembled. The fastener 30 can extend at least partially through an aperture 44 into the recess 40 and can engage the insert 28 along a head portion thereof. The fastener 30 can additionally extend to fasten to the tibial baseplate 24 along a threaded portion as illustrated and described subsequently. As will be further discussed subsequently, features of the insert 28, fastener 30, tibial baseplate 24 and tibial bearing component 26 reduce micro-motion of the tibial bearing component 26 relative to the tibial baseplate 24.

In addition to the proximal surface 42, the tibial baseplate 24 has a distal surface 46 configured to interface with and abut a resected surface of the tibia (not shown). The keel 36 extends generally distal of the distal surface 46 according to the example of FIGS. 1A and 1B. The keel 36 can be configured to be received in a corresponding recess within the tibia to facilitate fixation of the tibial baseplate 24 to the tibia. However, according to other examples the tibial baseplate 24 can use additional or other features (i.e. features additional to or other than the keel 36) to facilitate fixation to the tibia including bone cement, spikes, augments and/or pegs. Thus, the keel 36 and stem 38 need not be utilized in all examples.

Figure 2:
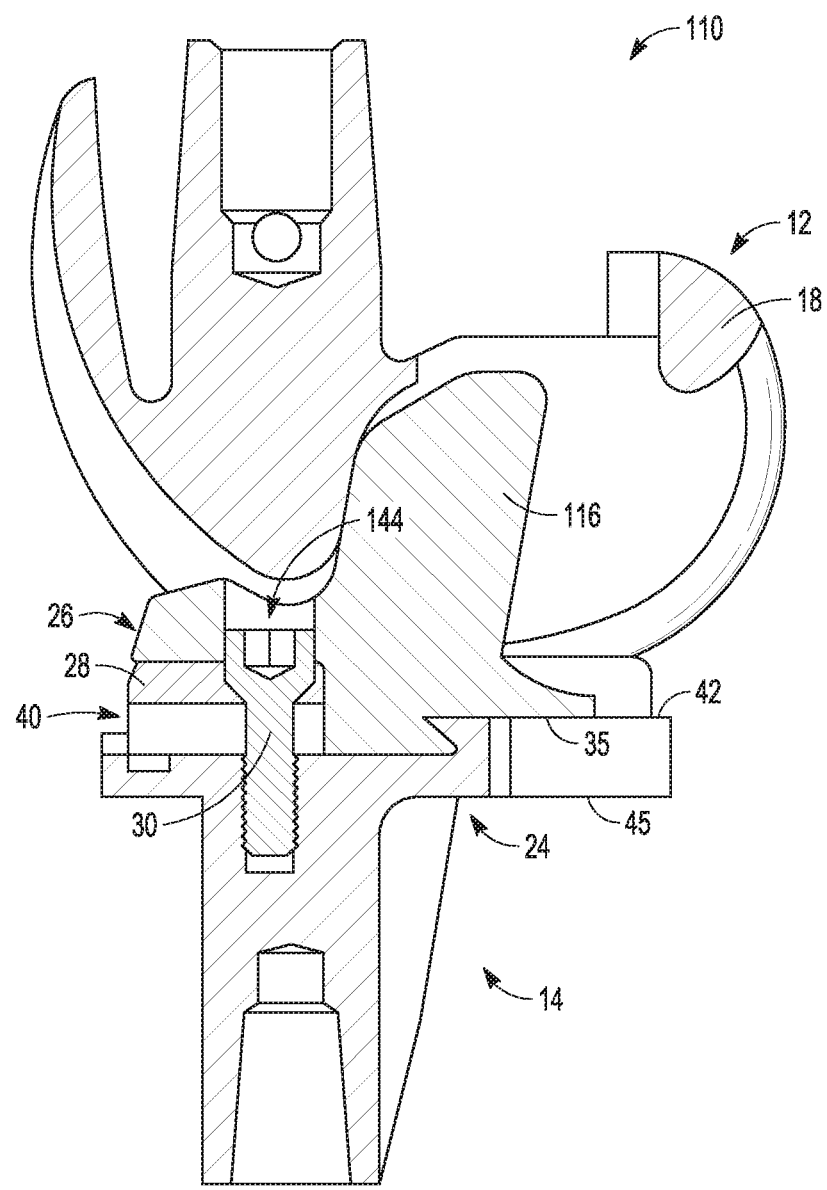
FIG. 2 shows a cross-sectional view of another example of the prosthesis assembly but with the femoral component moved to an extension position rather than the 135° flexion position previously illustrated according to an example of the present application.

FIG. 2 shows a second example of a prosthesis assembly 110 of similar construction to the prosthesis assembly 10 of FIGS. 1A and 1B. However, in FIG. 2 the location of the aperture 144 has been altered relative to the aperture 44. The aperture 144 does not pass through the spine 116 in the embodiment of FIG. 2 but is disposed anterior thereof. In contrast, the aperture 44 passed through an anterior portion of the spine 16 as shown in FIGS. 1A and 1B. Thus, it is contemplated that the aperture 44, 144 can be disposed in a plurality of positions including passing through at least a portion of the spine, anterior of the spine or posterior of the spine.

FIG. 2 additionally shows the femoral prosthesis 12 articulated to an extension position relative to the tibial prosthesis 14. In such position, the cam 18 can be disposed out of contact with the spine 116.

Thus, as shown in one or more of FIGS. 1A, 1B and 2, the tibial bearing component 26 can have medial and lateral proximal articular surfaces 32, 34 (FIG. 1A) and an opposing distal surface 35 (FIG. 2). The tibial bearing component 26 can define at least one recess 40 therein with the recess 40 having an opening at a periphery of the tibial bearing component 26. The tibial baseplate 24 can be coupled to the tibial bearing component 26 on the proximal surface 42 thereof and having a distal surface 45 configured to be disposed on a resected proximal surface of a tibia. The insert 28 can be configured to be disposed within the recess 40 and can engage the tibial baseplate 24 and the tibial bearing component 26. The fastener 30 can be insertable into the tibial bearing component 26 and can be configured to retain the insert 28 to the tibial baseplate 24.

Figure 3A:
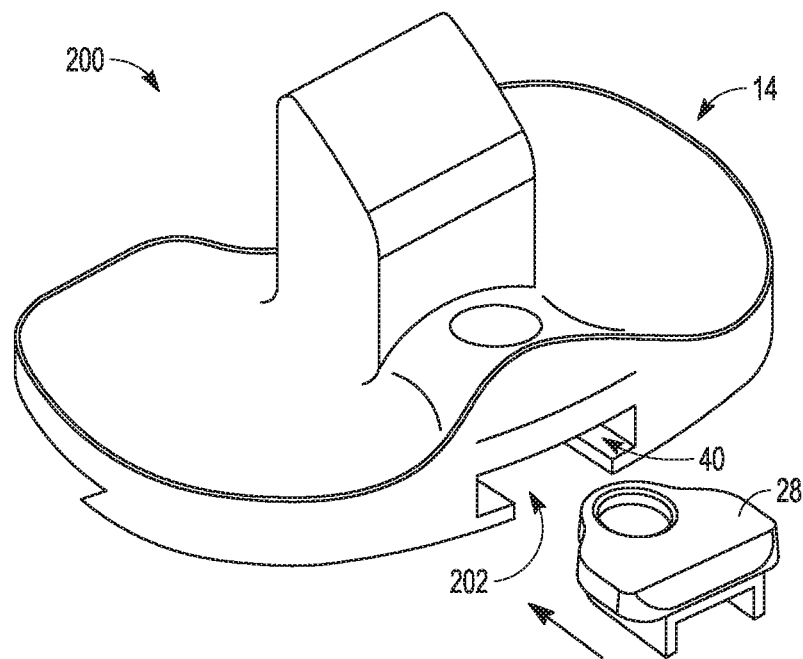
FIGS. 3A-3D illustrate a method of assembly for a tibial prosthesis according to an example of the present application.
Figure 3B:
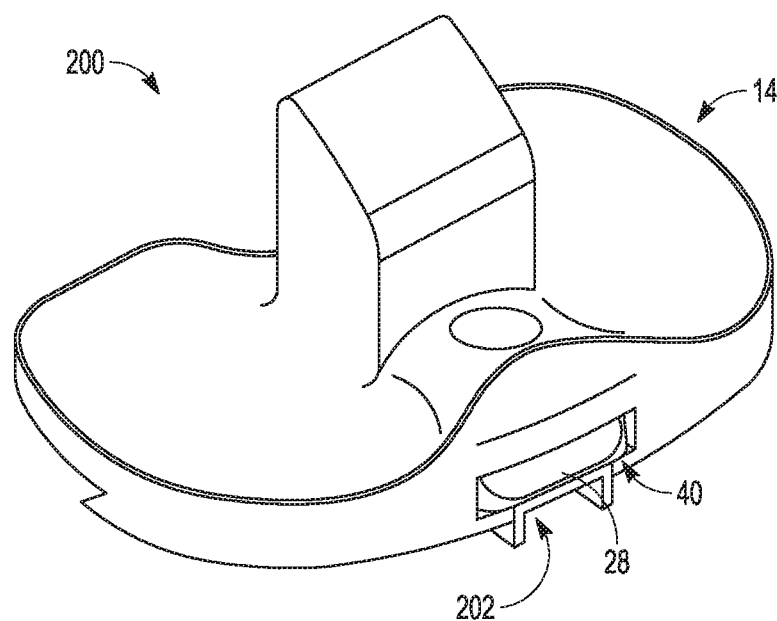

FIGS. 3A-3D illustrate a method 200 by which the tibial prosthesis 14 can be assembled. The method 200 includes passing the insert 28 through a peripheral opening 202 and into the recess 40 formed in the tibial bearing component 26 as shown in FIGS. 3A and 3B. The method engages a portion (e.g., tab 306 in FIG. 5) of the insert 28 with the tibial bearing component 26 while having first and second wings (described and number subsequently in reference to FIGS. 4A-5B) of the insert 28 received in corresponding grooves (described and number subsequently in reference to FIG. 4A) that are part of the recess 40. A tool can be used in some instances to facilitate passing the insert 28 and engagement as described above. The tool can also facilitate removal of the insert 28 from the recess 40 in some examples.

Figure 3C:
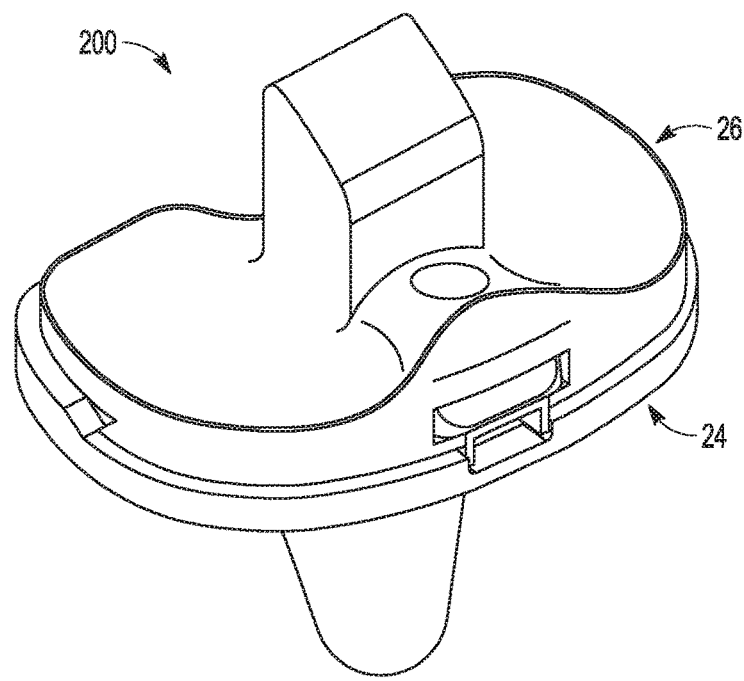

The method 200 can engage the tibial bearing component 26 with the tibial baseplate 24 as shown in FIG. 3C. This can initially be accomplished with engagement features such as dovetail boss, rails, notches or the like as will be illustrated and described subsequently. The insert 28 can be fastened to the tibial baseplate 24 as is initially demonstrated in FIG. 3D by passing the fastener 30 through the aperture 144 and into the recess 40 to engage the insert 28. The fastener 30 can then be rotated to thread with the tibial baseplate 24 to secure the insert 28 to the tibial baseplate 24 and thereby secure the tibial bearing component 26 to the tibial baseplate 24.

Figure 3D:
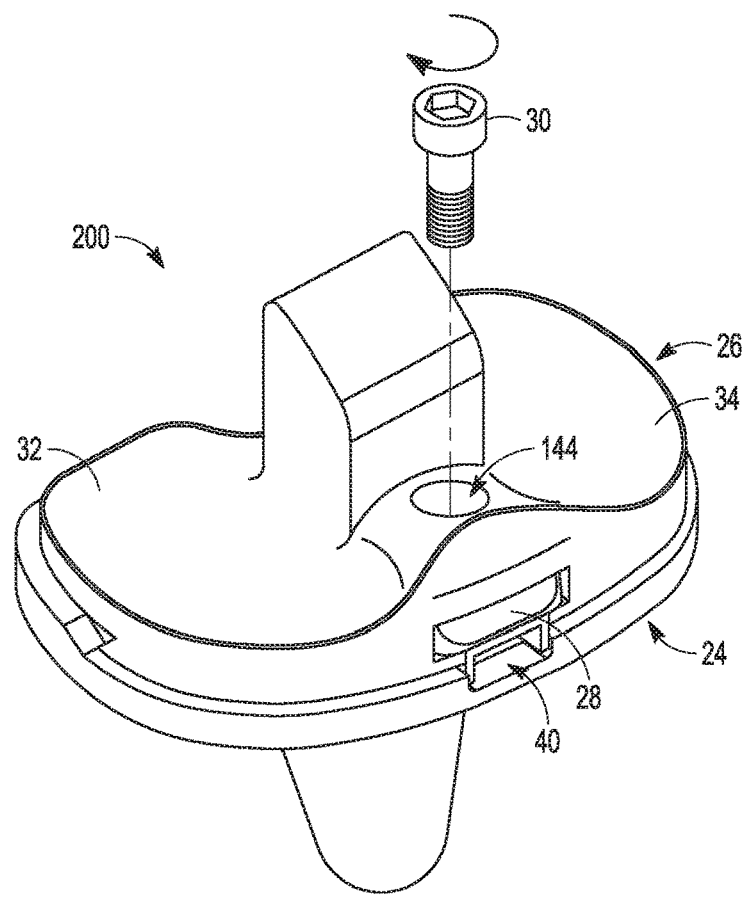

As will be discussed and illustrated in reference to further FIGURES subsequently, fastening the insert 28 to the tibial baseplate 24 can include passing the fastener 40 through a region located between medial and lateral proximal articular surfaces 32, 34 of the tibial bearing component 26 (the location of the aperture 144) as shown in FIG. 3D. The method 200 can also engage a first foot of the insert with a first portion of a rail of the tibial baseplate and can engage a second foot of the insert with a second portion of the rail of the tibial baseplate as will be discussed subsequently in reference to FIGS. 4 and 4A.

Figure 4:
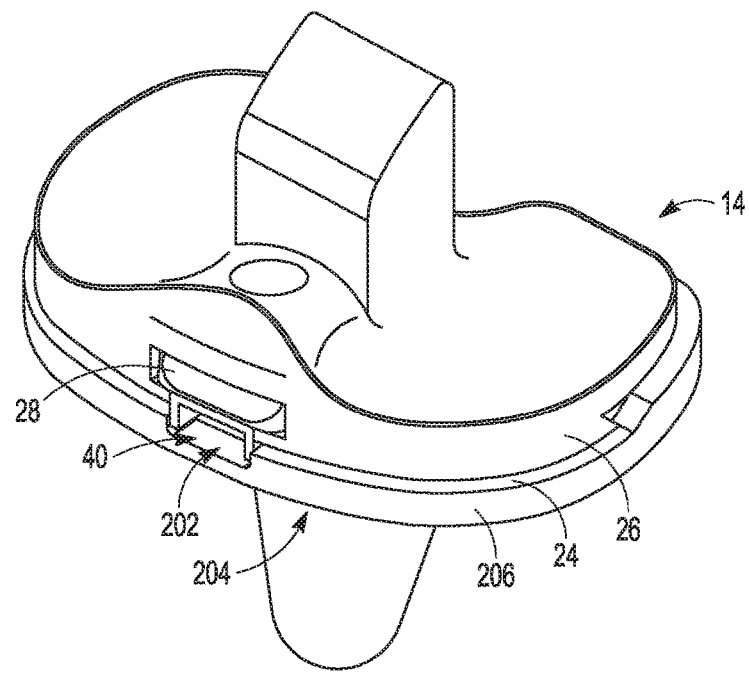
FIG. 4 shows the tibial prosthesis after having undergone the assembly previously illustrated in FIG. 3.
Figure 4A:
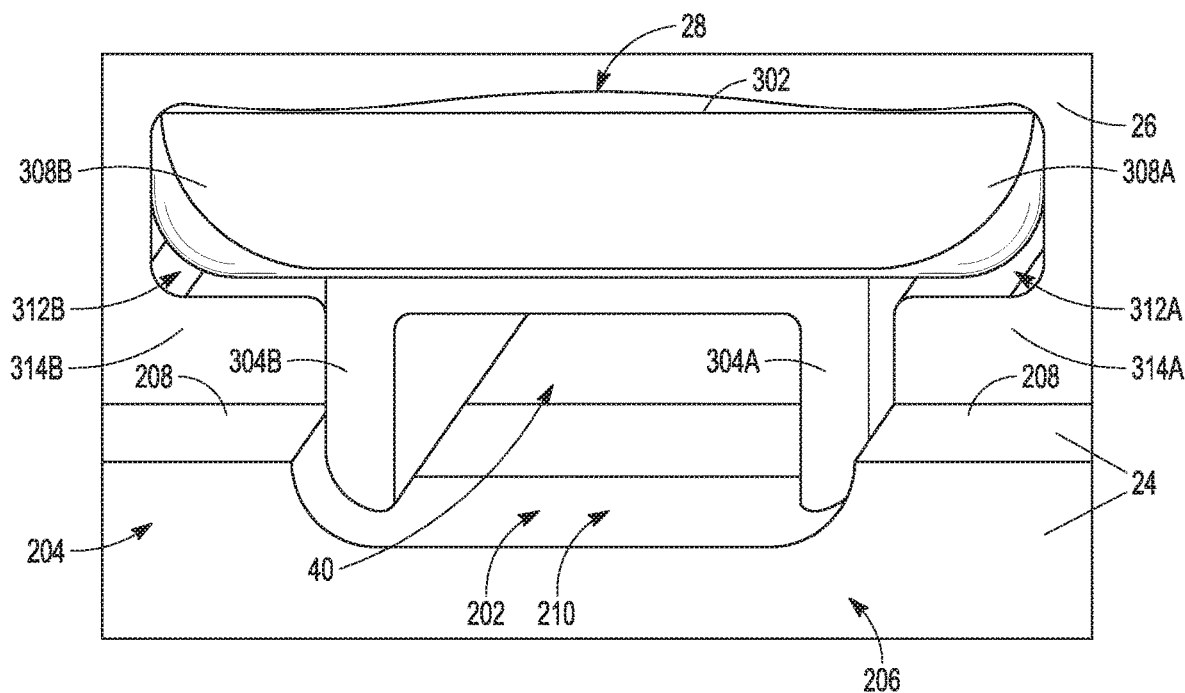
FIG. 4A shows an enlargement of a portion of the tibial prosthesis further illustrating the insert engaging portions of the tibial baseplate according to an example of the present application.

FIG. 4 shows the assembled tibial prosthesis 14. FIG. 4A is an enlarged view of an anterior portion of the tibial baseplate 24, the tibial bearing component 26 and the insert 28.

Figure 5:
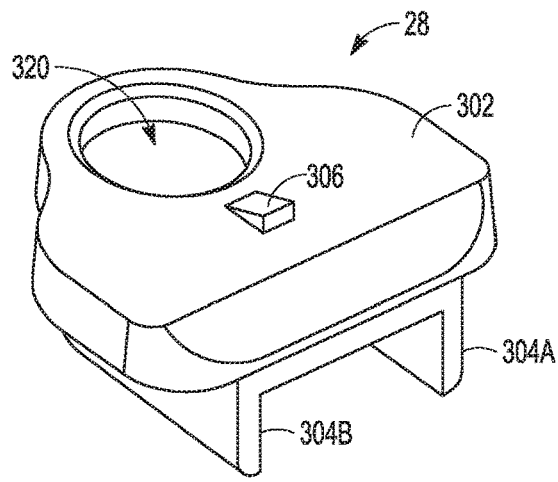
FIG. 5 show a perspective view of the insert according to an example of the present application.
Figure 5A:
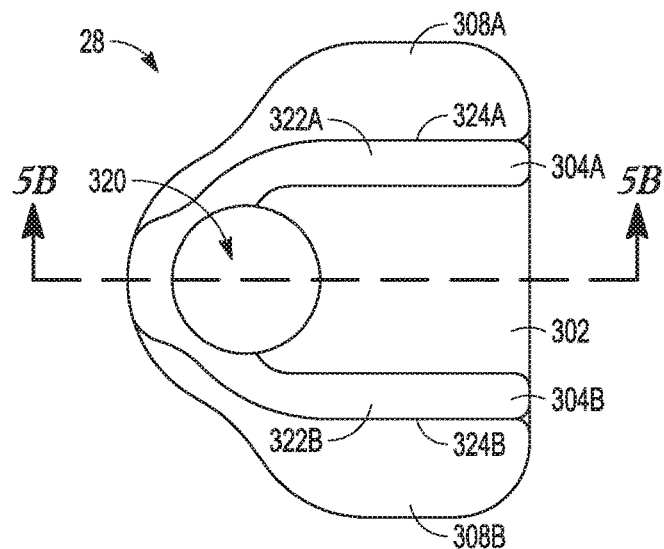
FIG. 5A shows a plan view of a distal portion of insert including first and second feet and an aperture according to an example of the present application.
Figure 5B:
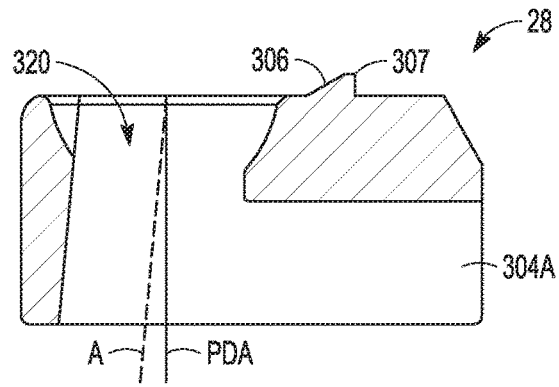
FIG. 5B is a cross-sectional view of the insert along line 5B-5B of FIG. 5A.

As is best shown in FIG. 4A, the insert 28 can be positioned in the recess 40 and can be configured to engage portions of the tibial baseplate 24. More particularly, the insert 28 can include a body 302, a first foot 304A and a second foot 304B as shown in FIGS. 4A, 5 and 5A. A tab 306 can project proximal of the body 302 as shown in FIGS. 5 and 5B. The body 302 can include first and second wings 308A and 308B that extend outward of the first foot 304A and second foot 304B, respectively. According to one example, the first wing 308A extends lateral of the first foot 304A and the second wing 308B extends medial of the second foot 304B.

As shown in FIGS. 4 and 4A, the opening 202 can be located at an anterior portion 204 of a periphery 206 of the tibial bearing component 26. The insert 28 can be disposed in the recess 40 such that substantially an entirety or all of the insert 28 is disposed therein. Additionally, when disposed in the recess 40, substantially an entirety of the insert 28 can be disposed anterior of the fastener 30 (FIGS. 1B and 2).

As shown in FIG. 4A, the tibial baseplate 24 can include a rail 208 extending from the proximal surface 42 along the periphery 206. The rail 208 has a gap 210. The gap 210 can be part of the opening 202, and therefore, can comprise part of the recess 40. In some examples, part of the rail 208 and gap 210 can be disposed anterior of the recess 40 and opening 202. The example of FIG. 4A illustrates that with the insert 28 disposed in the recess 40, at least a portion of the insert 28 extends into the gap 210 and engages the rail 208 (e.g. along the medial and lateral side surfaces of the first foot 304A and second foot 304B as shown subsequently in FIGS. 5 and 5A). Such engagement, along with engagement of the insert 28 against the proximal surface 42, can limit micro-motion of the tibial bearing component 26 relative to the tibial baseplate 24 with securement of the fastener 30.

As shown in FIG. 4A, the first and second wings 308A and 308B are configured to be received in corresponding grooves 312A and 312B that are part of the recess 40. The grooves 312A and 212B are shaped similar to the wings 308A and 308B. The wings 308A and 308B can be disposed on and engage projections 314A, 314B that form a distal portion of the grooves 312A and 312B.

Turning to FIGS. 5-5B, the body 302 can have an aperture 320 defined thereby. The aperture 320 can be configured to receive a head of the fastener 30 as was previously illustrated in FIGS. 1B and 2. More particularly, according to some examples the aperture 320 can be hemispherical in shape along a portion thereof so as to facilitate centering of the fastener 30 during insertion. The hemispherical shape can also minimize stretch loss of the fastener 30 due to settling of the fastener 30 during use. In some examples, such as that of FIG. 5B, an axis A of the aperture 320 can be angled relative to a proximal-distal axis PDA of the insert 28. This causes the fastener 30 to be angled in a direction in addition to the proximal-distal direction such as the anterior-posterior direction.

The first foot 304A can be connected to the body 302 and can extend distal therefrom in a direction generally perpendicular to that of wing 308A. As shown in FIG. 5A, in addition to a distal surface 322A, the first foot 304A can have a lateral side surface 324A engaging the tibial baseplate 24 when assembled as illustrated and described above in reference to FIG. 4A. Similarly, the second foot 304B can be connected to the body 302 and can extend distal therefrom. The second foot 304B can be spaced from the first foot 304A. The second foot 304B can have a distal surface 322B and can have a medial side surface 324B engaging the tibial baseplate 24 when assembled as illustrated and described above in reference to FIG. 4A.

The tab 306 can extend proximally from the body 304 and can engage the tibial bearing component 26 to temporarily retain the insert 28 within the tibial bearing component 26 such as illustrated in FIG. 3B of the method 200. More particularly, the tab 306 has an anterior face 307 (FIG. 5B) that engages a corresponding surface of the tibial bearing component 26 so as not to allow the insert 28 to be withdrawn from the recess 40 such as in the posterior-to-anterior direction (an opposing direction to the direction of insertion of the insert 28 into the recess 40 as shown in FIG. 3A).

Figure 6:
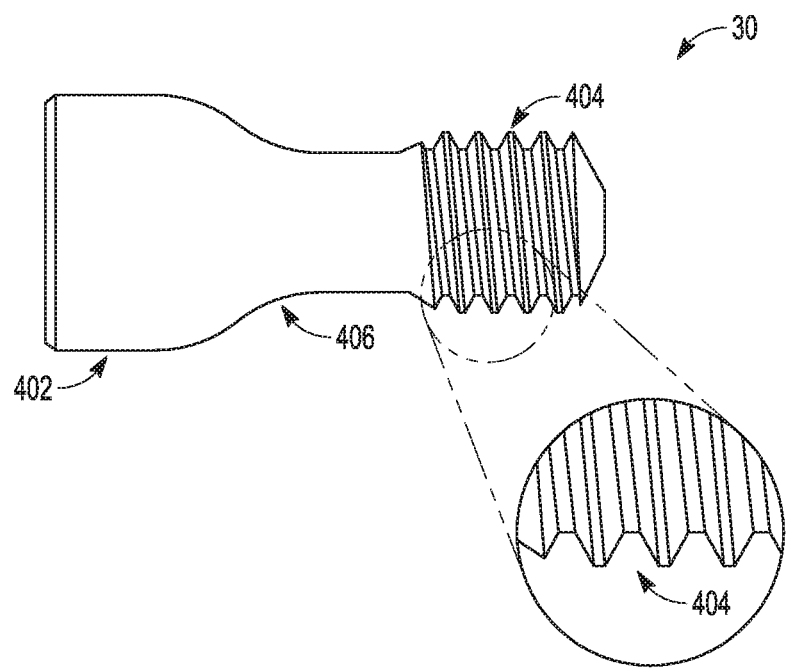
FIG. 6 is a plan view of the fastener according to an example of the present application.

FIG. 6 shows an example of the fastener 30 in greater detail. The fastener 30 can have a head portion 402 and a threaded portion 404. FIG. 6 provides an enlargement of the threaded portion 404. As discussed with regard to the insert 28 of FIGS. 5-5B, the head portion 402 can share as a similar curvature as the aperture 320. For example, the head portion 402 can be provided with a hemispherical configuration similar to that of the aperture 320 so as to facilitate centering of the screw during insertion (e.g. the conformity of the hemispherical head and the insert can be anywhere between a 1:1 and a 1:1.2 ratio, inclusive). Such configuration can also minimize stretch loss due to the fastener settling. A neck region 406 between the head portion 402 and the thread portion can have a necked down area with a diameter smaller than a minor diameter of the threaded portion 404. This can prevent notching of the neck region 406 during fabrication.

As shown in FIG. 6, the threaded portion 404 can include rounded root radii and the minor diameter can be relative to a major diameter to improve the strength of the fastener relative to that of a standard thread.

Figure 7:
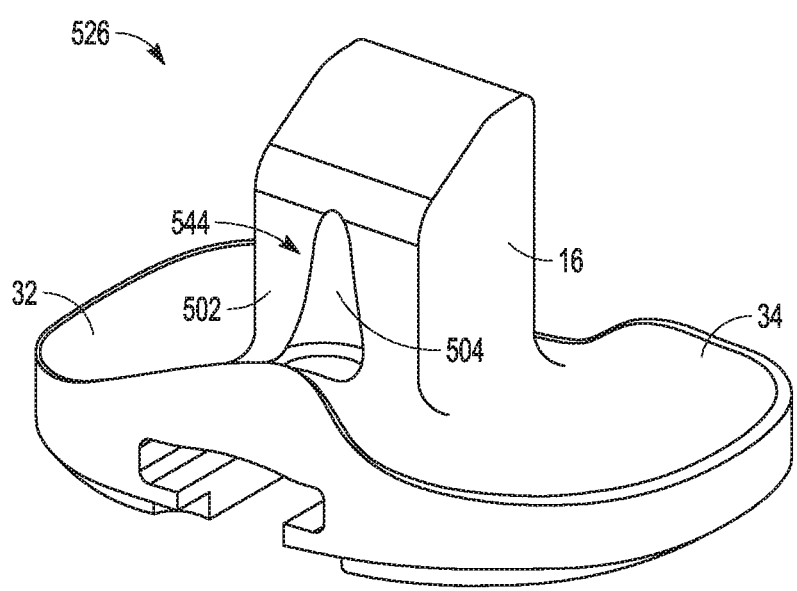
FIGS. 7-7C show the tibial bearing component from various perspectives according to an example of the present application.
Figure 7A:
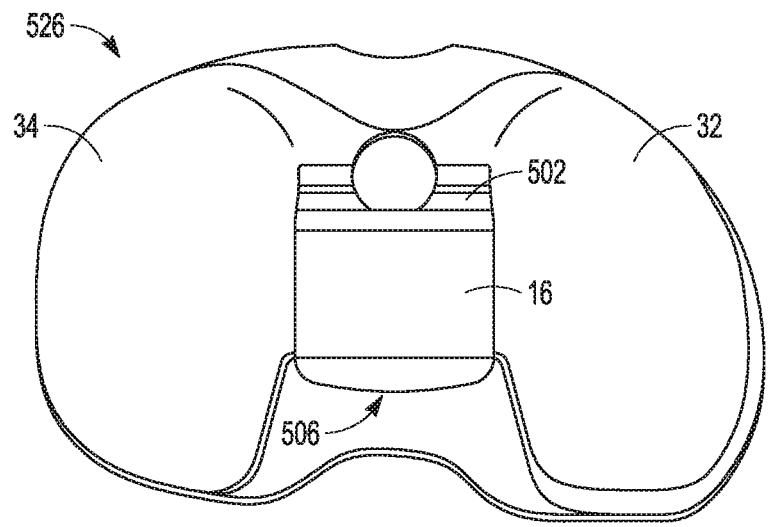
Figure 7B:
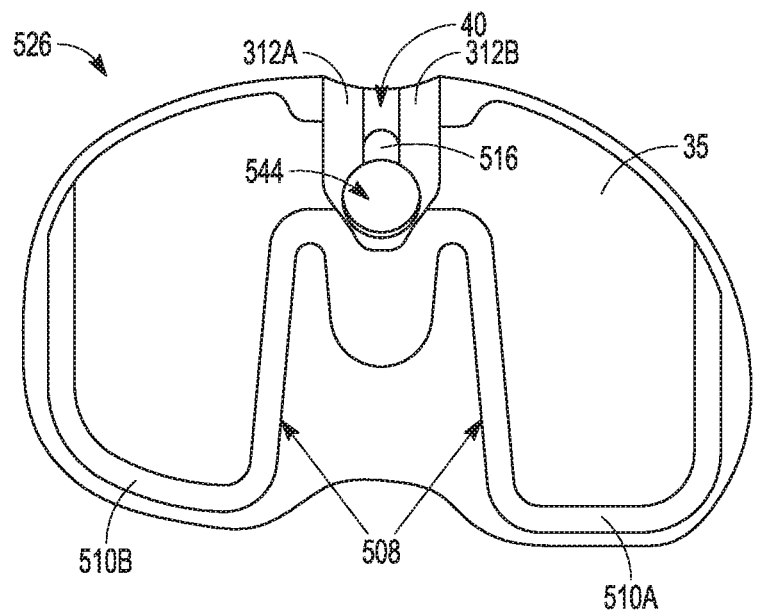
Figure 7C:
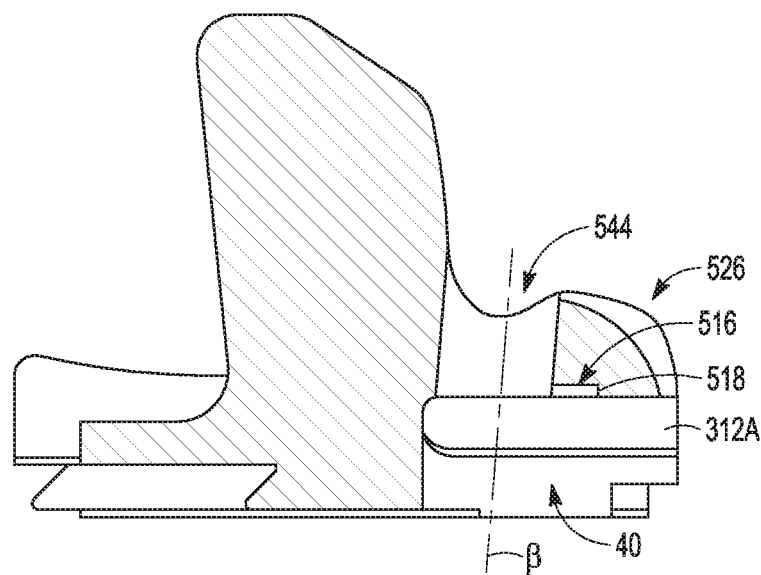

FIGS. 7-7C show a tibial bearing component 526 similar in construction to that of tibial bearing component 26 save that the disposition of an aperture 544 such so as to extend through at least an anterior portion of the spine 16. Thus, an anterior portion 502 of the spine 16 has a cut-out 504 as shown in FIG. 7. All other features of the tibial bearing component 526 are similar to or identical to those of the tibial bearing component 26 as previously described.

As shown in FIG. 7A, the spine 16 can be centrally located between the medial articular surface 32 and the lateral articular surface 34. A posterior region 506 of the spine 16 can have a radius such that the posterior region 506 is convexly shaped in a medial-lateral direction when viewed in a transverse plane. In contrast, the anterior portion 502 can be substantially flat when viewed in the transverse plane.

FIG. 7B shows a plan view of the distal surface 35 of the tibial bearing component 526. FIG. 7B additionally shows the recess 40. It should be noted that although the recess 40 and corresponding insert 28 are shown positioned at the anterior region and extending to an anterior periphery of the tibial bearing component 26 and the tibial baseplate 24 in the examples provided, in other embodiments the recess 40 and insert 28 can be disposed in other locations of the tibial bearing component 26 and the tibial baseplate 24. Additionally, although a substantially anterior-posterior insertion direction for the insert 28 into the recess 40 was illustrated and described, in other examples the insertion direction can be in another direction (e.g., medial-lateral, proximal-distal) or combinations of directions (e.g., medial-lateral and anterior-posterior).

Figure 8A:
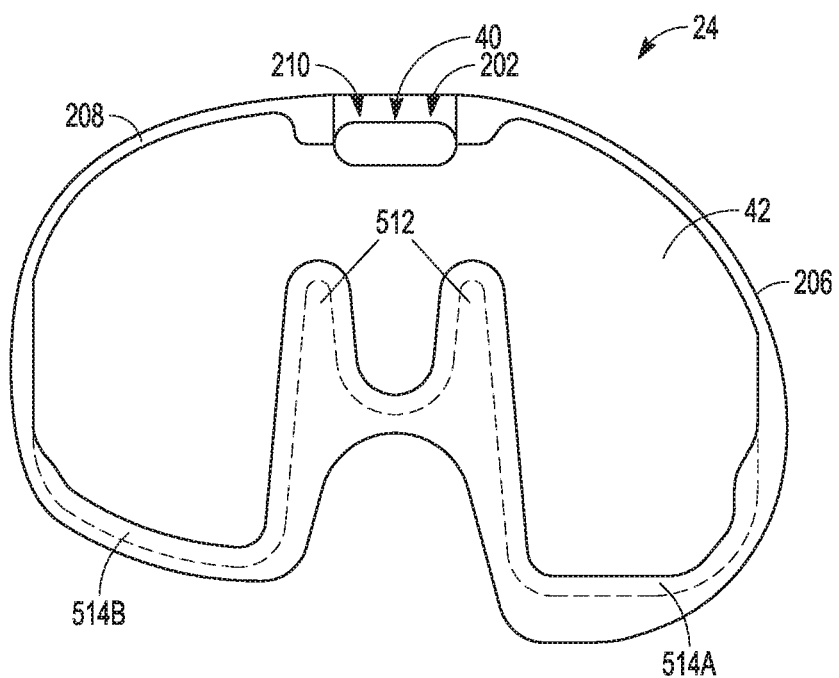
FIGS. 8A and 8B show the tibial baseplate from various perspectives according to an example of the present application.

FIG. 7B also illustrates additional connection mechanisms such as a double dovetail notch 508 and peripheral notches 510A and 510B these features are configured to attach to a double dovetail boss 512 and undercut rails 514A, 514B, respectively of the tibial baseplate 24 as shown in FIG. 8A. Upon assembly, the tibial bearing component 26, 126, 526 can be advanced along a path, such that tibial bearing component 26, 126, 526 moves along a generally anterior-to-posterior path as the double dovetail notch 508 begins to engage with the double dovetail boss 512 and the peripheral notches 510A and 510B begin to engage with the undercut rails 514A, 514B. Further posterior movement of the tibial bearing component 212 causes a tight interfitting engagement between these features. As is discussed and illustrated further in reference to FIG. 3, further engagement and securement of the tibial bearing component 26, 126 526 to the tibial baseplate 24 is facilitated by the insert 28 and the fastener 30.

As was previously shown in reference to FIGS. 1B and 2, the aperture 44, 144, 544 can be configured to receive at least a portion of the fastener 30 (FIGS. 1B and 2) therein. Indeed, upon assembly a head portion of the fastener 30 may remain in the aperture 44, 144, 544. According to the example of FIG. 7C, the aperture 544 can be angled (along axis B) relative to a proximal-distal axis (not shown) of the tibial bearing component 526 such that the aperture 544 extends both proximal-distal and anterior-posterior. The angle can be in a manner similar or identical to that provided for the aperture 320 of the insert 28 as previously discussed. In other examples, the aperture and/or aperture of the insert 28 can be angled in any manner desired not just in the proximal-distal and anterior-posterior manner illustrated.

FIGS. 7B and 7C illustrate the recess 40 in further detail including the grooves 312A and 312B (FIG. 7B). FIGS. 7B and 7C also show a notch 516 that can form a part of the recess 40. The notch 516 can be positioned anterior of the aperture 544 along a proximal portion of the recess 40. The notch 516 is configured to receive the tab 306 (FIGS. 5 and 5B) when the insert 28 is received in the recess 40. An anterior surface 518 that forms a part of the notch 516 is configured to engage the anterior face 307 (FIG. 5B) of the insert 28. This engagement can temporarily restrict movement of the insert 28 such that the insert cannot easily be withdrawn from the recess 40 such as in the posterior-to-anterior direction (an opposing direction to the direction of insertion of the insert 28 into the recess 40 as shown in FIG. 3A).

Figure 8B:
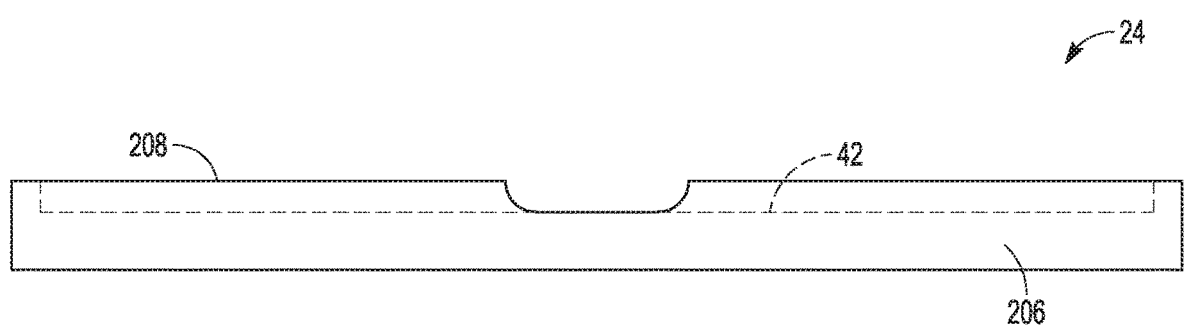

FIGS. 8A and 8B show the tibial baseplate 24. In particular, FIG. 8A shows the proximal surface 42 of the tibial baseplate 24. FIG. 8B shows a plan view of a proximal portion of the tibial baseplate 24. Additional features shown include the rail 208 extending from the proximal surface 42 along the periphery 206. The rail 208 has the gap 210 as previously discussed in reference to FIG. 4A. The gap 210 can be part of the opening 202, and therefore, can comprise part of the recess 40. As shown in FIG. 8A, the tibial baseplate 24 can also include the double dovetail boss 512 and the undercut rails 514A, 514B as previously discussed.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 CFR. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A method of assembling a tibial prosthesis for a knee arthroplasty, the method comprising: providing a tibial bearing component having medial and lateral proximal articular surfaces and an opposing distal surface, wherein the tibial bearing component defines a peripheral opening between the medial and lateral proximal articular surfaces and the distal surface; passing an insert through the peripheral opening and into a recess formed in a tibial bearing component; engaging a portion of the insert with the tibial bearing component while having wings of the insert received in corresponding grooves that are part of the recess; engaging the tibial bearing component with a tibial baseplate; fastening the insert to the tibial baseplate; and wherein fastening the insert to the tibial baseplate includes passing a fastener through a proximal surface region located between medial and lateral proximal articular surfaces of the tibial bearing component.

2. The method of claim 1, further comprising engaging a first foot of the insert with a first portion of a rail of the tibial baseplate and engaging a second foot of the insert with a second portion of the rail of the tibial baseplate.

3. A tibial prosthesis for a knee arthroplasty comprising:
a tibial bearing component having medial and lateral proximal articular surfaces and an opposing distal surface, wherein the tibial bearing component defines at least one recess therein with the recess having an opening at a periphery between the medial and lateral proximal articular surfaces and the distal surface of the tibial bearing component;
a tibial baseplate configured to couple to the tibial bearing component on a proximal surface thereof and having a distal surface configured to be disposed on a resected proximal surface of a tibia;
an insert insertable within the recess through the opening and having wings that engage the tibial bearing component and one or more projections that engage the tibial baseplate; and
a fastener retaining the insert to the tibial baseplate and passing through the insert.

4. The tibial prosthesis of claim 3, wherein the tibial bearing component comprises a posterior-stabilized tibial bearing component with a spine disposed between the medial and lateral proximal articular surfaces.

5. The tibial prosthesis of claim 3, wherein the insert comprises:
a body having an aperture defined thereby, the aperture receives a head of the fastener; and
the one or more projections comprise:
a first foot connected to the body and extending distal therefrom, the first foot having a first side surface engaging the tibial baseplate; and
a second foot connected to the body and extending distal therefrom, the second foot spaced from the first foot and having a second side surface engaging the tibial baseplate.

6. The tibial prosthesis of claim 5, wherein the insert further comprises a tab extending proximally from the body, the tab engaging the tibial bearing component to retain the insert within the tibial bearing component.

7. The tibial prosthesis of claim 5, wherein the head of the fastener and the aperture share a similar curvature such the fastener is self-centering within the insert.

8. The tibial prosthesis of claim 3, wherein the wings comprise a first wing that extends lateral of a first foot extending from a body and a second wing that extends medial of a second foot extending from the body.

9. The tibial prosthesis of claim 3, wherein the opening is at an anterior portion of the periphery of the tibial bearing component and the insert is disposed in the recess such that substantially an entirety of the insert is disposed anterior of the fastener.

10. The tibial prosthesis of claim 3, wherein the tibial baseplate includes a rail extending from the proximal surface along a periphery thereof, wherein the rail has a gap in a region of the recess, and wherein with the insert disposed in the recess, at least a portion thereof extends into the gap and engages the rail to limit micro-motion of the tibial bearing component.

11. The tibial prosthesis of claim 3, further comprising a second aperture formed in the tibial bearing component and extending from between the medial and lateral proximal articular surfaces to communicate with the recess, wherein the second aperture is configured to receive at least a portion of the fastener, and wherein the second aperture is angled relative to a proximal-distal axis of the tibial bearing component such that second aperture extends both proximal-distal and anterior-posterior.

12. A system for use in a knee arthroplasty comprising:
a tibial bearing component having medial and lateral proximal articular surfaces and an opposing distal surface, wherein the tibial bearing component defines at least one recess therein with the recess having an opening at a periphery between the medial and lateral proximal articular surfaces and the distal surface of the tibial bearing component;
a tibial baseplate configured to receive the tibial bearing component on a proximal surface thereof and having a distal surface configured to be disposed on a resected proximal surface of a tibia;
an insert disposable through the opening and into the recess, the insert having a plurality of projections to engage the tibial baseplate and the tibial bearing component when the insert, the tibial baseplate and the tibial bearing component are assembled together; and
a fastener insertable into the tibial bearing component and the insert and configured to retain the insert to the tibial baseplate.

13. The system of claim 12, wherein the tibial bearing component comprises a posterior-stabilized tibial bearing component with a spine disposed between the medial and lateral proximal articular surfaces, and wherein the fastener is insertable into an anterior portion of the spine.

14. The system of claim 12, wherein the insert comprises:
a body having an aperture defined thereby, the aperture configured to receive a head of the fastener; and
wherein at least some of the projections include:
a first foot extending generally distal from the body and having a first side surface engaging the tibial baseplate; and
a second foot extending generally distal from the body and spaced from the first foot, the second foot having a second side surface engaging the tibial baseplate.

15. The system of claim 14, wherein one of the projections comprises a tab extending proximally from the body and configured to engage the tibial bearing component to retain the insert within the tibial bearing component.

16. The system of claim 12, wherein some of the projections comprise a first wing that extends lateral of a first foot and a second wing that extends medial of a second foot.

17. The system of claim 12, wherein a head of the fastener and an aperture of the insert share a similar curvature such the fastener is self-centering within the insert when inserted therein.

18. The system of claim 12, wherein the opening is at an anterior portion of the periphery of the tibial bearing component and the insert is disposed in the recess when assembled such that substantially an entirety of the insert is disposed anterior of the fastener.

19. The system of claim 12, wherein the tibial baseplate includes a rail extending from the proximal surface along a periphery thereof, wherein the rail has a gap in a region of the recess and forms a part of the opening, and wherein with the insert disposed in the gap the insert is configured to engage the rail to limit micro-motion of the tibial bearing component.

20. The system of claim 12, further comprising a second aperture formed in the tibial bearing component and extending from the medial and lateral proximal articular surfaces to communicate with the recess, wherein the second aperture is configured to receive at least a portion of the fastener, and wherein the second aperture is angled relative to a proximal-distal axis of the tibial bearing component such that second aperture extends both proximal-distal and anterior-posterior.

* * * * *